United States Patent [19]

Imaki et al.

[11] Patent Number: 5,017,610

[45] Date of Patent: May 21, 1991

[54] DERIVATIVES OF P-SUBSTITUTED PHENYL ESTER OF PIVALIC ACID

[75] Inventors: Katsuhiro Imaki; Yoshinobu Arai; Tadao Okegawa, all of Osaka, Japan

[73] Assignee: Ono Pharmaceutical Co., Ltd., Osaka, Japan

[21] Appl. No.: 364,994

[22] Filed: Jun. 12, 1989

[30] Foreign Application Priority Data

Jun. 13, 1988 [JP] Japan .................. 63-145450
Mar. 6, 1989 [JP] Japan .................. 1-53541

[51] Int. Cl.$^5$ .......................... A61K 31/22
[52] U.S. Cl. ........................ 514/546; 544/158; 544/90; 544/92; 544/177; 546/216; 546/309; 546/312; 548/252; 548/337; 548/495; 548/539; 548/542; 549/362; 560/12; 560/13; 560/34; 560/138; 560/10; 560/142
[58] Field of Search ............ 560/142; 514/546

[56] References Cited

U.S. PATENT DOCUMENTS 3,793,292  2/1974  Yamamura et al. ............. 260/471
4,188,390  2/1980  Campbell ........................ 424/251

FOREIGN PATENT DOCUMENTS 2109842  9/1972  Fed. Rep. of Germany.
2136980  9/1984  United Kingdom.

Primary Examiner—Michael L. Shippen
Attorney, Agent, or Firm—Stevens, Davis, Miller & Mosher

[57] ABSTRACT

A derivative of general formula:

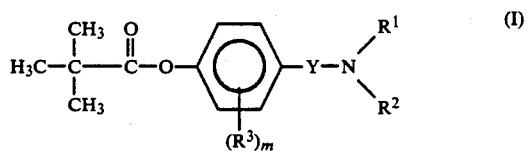

wherein Y is —SO$_2$— or

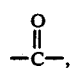

(i) $R^1$ and $R^2$, which may be the same or different, each represent, (1) —H, (2) C1-16 alkyl or (3) the formula: —X— A —(R$^4$)$_n$ wherein X is a single-bond, —SO$_2$—, C1-4 alkylene, C1-4 alkylene substituted by

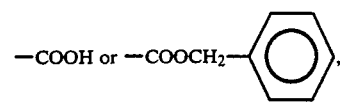

— A — is carbocyclic or heterocyclic ring, n is 1~5, $R^4$ is (1) —H or C1-8 alkyl, (2) C1-14 alkoxy, (3) C1-6 alkylthio, (4) —OH, halogen, —NO$_2$ or trihalomethyl, (5) the formula: —NR$^{41}$R$^{42}$ wherein R$^{41}$ and R$^{42}$ each represents halogen or C1-4 alkyl, (6) tetrazole, (7) —SO$_3$H or —CH$_2$OH, (8) the formula: —SO$_2$NR$^{41}$R$^{42}$ (9) the formula: —Z$^4$1—COOR$^{43}$ wherein Z$^{41}$ is single-bond, C1-4 alkylene or C2-4 alkenylene, R$^{43}$ is —H, C1-4 alkyl or benzyl, (10) the formula: —CONR$^{41}$R$^{42}$ (11) the formula: —COO—Z$^{42}$—COOR$^{43}$ wherein Z$^{42}$ is C1-4 alkylene, R$^{43}$ is —H, C1-4 alkyl or benzyl, (12) the formula: —COO—Z$^{42}$—CONR$^{41}$R$^{42}$ (13) the formula: —OCO—R$^{45}$ wherein R$^{45}$ is C1-8 alkyl or p-guanidinophenyl, (14) the formula: —CO—R$^{46}$ wherein R$^{46}$ is C1-4 alkyl, (15) the formula: —O—Z$^{43}$—COOR$^{450}$ wherein Z$^{43}$ is C1-6 alkylene, R$^{450}$ represents a hydrogen, C1-8 alkyl or p-guanidinophenyl, (16) the formula:

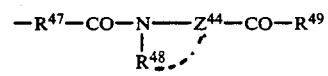

wherein

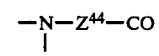

is an amino acid residue, $R^{47}$ is bond, C1-4 alkyl, $R^{48}$ is —H or C1-4 alkyl, $R^{49}$ is —OH, C1-4 alkoxy, —NH$_2$, amino substituted by one or two C1-4 alkyl, carbamoylmethoxy or carbamoylmethoxy substituted by one or two C1-4 alkyl at N atom of carbamoyl, wherein

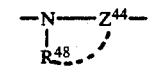

is C3-6 heterocyclic ring,
(ii) $R^1$, $R^2$ and N atom bonded to $R^1$ and $R^2$ together represents heterocyclic ring containing at least a N atom(s) and substituted by —COOH or unsubstituted heterocyclic ring containing at least a N atom(s), $R^3$ is (1) —H, (2) —OH, (3) C1-6 alkyl, (4) halogen, (5) C1-4 alkoxy or (6) C2-5 acyloxy, m is 1-4.

or non-toxic salt or an acid addition salt thereof possess inhibitory activity on elastase, and therefore is useful for treating and/or preventing agent for pulmonary emphysema, atherosclerosis and rheumatoid arthritis and the like.

3 Claims, No Drawings

DERIVATIVES OF P-SUBSTITUTED PHENYL ESTER OF PIVALIC ACID

SUMMARY

This invention is related to the derivatives of p-substituted phenyl ester of pivalic acid having an inhibitory activity on elastase, of the general formula:

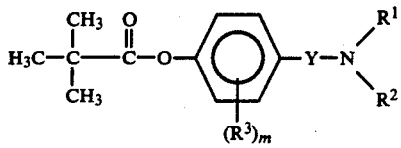

wherein $R^1$, $R^2$, $R^3$, Y and m have same meaning as described hereinafter.

BACKGROUND

Lysosomal hydrolases of neutrophils have an important role for an organism defense reaction against tissue damage caused by microbe or inflammation etc.

Elastase and cathepsin G, which belong to neutral serine proteinase locally existed in azurophil granule mainly play a part in decomposition of a connective tissue.

Especially, elastase degrades elastic connective tissue by cleaving the cross-linking of elastin which directly maintains the elasticity of lung tissue etc., and by cleaving hydrophobic part of protein [J. Cell. Biol., 40, 366 (1969)] and degrades the cross-linking area of collagen selectively as well as elastin [J. Biochem., 84, 559 (1978)], and it acts on tissue proteins such as proteoglycans etc. [J. Clin. Invest., 57, 615 (1976)]. Therefore, elastase plays an important role in metabolism of connective tissue.

Elastase is inactivated by $\alpha_1$-proteinase inhibitor ($\alpha_1$-PI) that is a common inhibitor for serine, proteinase in vivo and the unbalance of enzyme and inhibitor system causes the destruction of the tissue [Schweiz. Med. Wshr., 114, 895 (1984)].

The turnover of elastin in normal tissue is very slow [Endocrinology, 120, 92 (1978)], but the pathological acceleration in degradation of elastin is found under various unsound state such as pulmonary emphysema [Am. Rev. Respir. Dis., 110, 254 (1974)], atherosclerosis [Lab. Invest., 22, 228 (1970)] and rheumatoid arthritis [in Neutral Proteases of Human Polymorphonuclear Leukocytes, Urban and Schwarzenberg, Baltimore - Munich (1978), page 390], suggesting the relationship of elastase and diseases [Infection.Inflammation.Immunity, 13, 13 (1983)].

PRIOR ARTS

Under the background as mentioned above, recent studies and development on elastase inhibitors have been heartily conducted, and various substances inhibiting elastase have been proposed and many patent applications have been filed.

Particularly, recently, for example, in the specification of U.S. Pat. No. 4,683,241, the compound of the general formula:

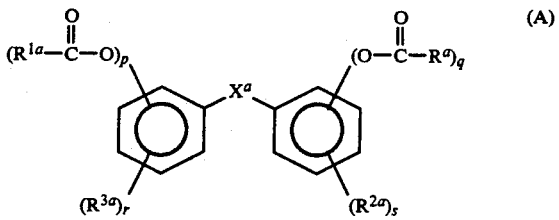

wherein Xa represents a group selected from carbonyl group, methylene group, oxygen atom, azo group, sulfonyl group, —CH(OH)—,

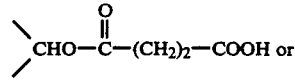

together with the benzene rings represents the group

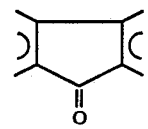

$R^a$ and $R^{1a}$ each represents an alkyl group and an acylaminoalkyl group of 2 to 6 carbon atoms, an alkoxy group, an alkenyl group and carboxyalkyl group of up to 6 carbon atoms, cycloalkyl group of 3 to 6 carbon atoms or an alkoxycarbonylalkyl group of up to 10 carbon atom(s), $R^{2a}$ and $R^{3a}$ represent hydroxy atom, halogen atom, pyranyloxy, an alkyl, an alkenyl, hydroxyalkyl and formylalkyl group of up to 4 carbon atom(s) or carboxyalkyl group of up to 6 carbon atom(s), was disclosed.

PURPOSE OF THE INVENTION

As the result of energetic investigations conducted in order to find new elastase inhibitory agents having quite different chemical structure from conventional ones, the present inventors have found that the compound of the general formula (I) achieves this purpose.

COMPARISON WITH THE PRIOR ARTS

In the specification of U.S. Pat. No. 4,683,241, benzoylphenyl ester and benzenesulfonylphenyl ester of any kind pivalic acid were disclosed as the inhibitory agent on elastase.

The structure of sulfamoylphenyl ester and carbamoylphenyl ester in the present invention can not be obvious from compounds of the Prior Art, and it have been unexpected that compounds of the present invention have inhibitory effect on elastase.

DISCLOSURE OF THE INVENTION

Accordingly, the present invention relates to the compounds of the general formula:

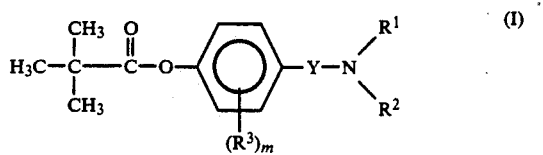

wherein Y represents sulfonyl (—SO₂—) group or carbonyl

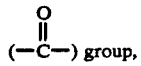 group, (i) R¹ and R², which may be the same or different, each represent
(1) hydrogen atom,
(2) an alkyl group of up to 16 carbon atom(s) or an alkyl group of up to 16 carbon atom(s) substituted by carboxy group
(3) a group of the formula: —X—Ⓐ—(R⁴)ₙ
wherein X represents single-bond, sulfonyl (—SO₂) group, an alkylene group of up to 4 carbon atom(s) or an alkylene group of up to 4 carbon atom(s) substituted by —COOH group or benzyloxycarbonyl

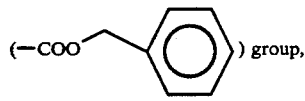 group,

—Ⓐ— represents carbocyclic ring or heterocyclic ring,
n represents an integer of 1 to 5,
R⁴ represents, same or different,
hydrogen atom or an alkyl group of up to 8 carbon atom(s),
an alkoxy group of up to 14 carbon atom(s),
an alkylthio group of up to 6 carbon atom(s),
hydroxy group, halogen atom, nitro group or trihalomethyl group,
a group of the formula: —NR⁴¹R⁴² wherein R⁴¹ and R⁴² each represents, same or different, hydrogen atom or alkyl group of up to 4 carbon atom(s),
tetrazole group,
sulfonic acid (—SO₃H) group or hydroxymethyl (—CH₂OH) group,
a group of the formula: —SO₂NR⁴¹R⁴² wherein R⁴¹ and R⁴² have the same meaning as described hereinbefore,
a group of the formula: —Z⁴¹—COOR⁴³ wherein Z⁴¹ represents single-bond, an alkylene group of up to 4 carbon atom(s) or an alkenylene group of from 2 to 4 carbon atoms,
R⁴³ represents hydrogen atom, an alkyl group of up to 4 carbon atom(s) or benzyl group,
a group of the formula: —CONR⁴¹R⁴² wherein R⁴¹ and R⁴² have same meaning as described hereinbefore,
a group of the formula: —COO—Z⁴²—COOR⁴³ wherein Z⁴² represents an alkylene group of up to 4 carbon atom(s),
R⁴³ represents hydrogen atom, an alkyl group of up to 4 carbon atom(s) or benzyl group,
a group of the formula: —COO—Z⁴²—CONR⁴¹R⁴² wherein Z⁴², R⁴¹ and R⁴² have same meaning as described hereinbefore.
a group of the formula: —OCO—R⁴⁵ wherein R⁴⁵ represents an alkyl group of up to 8 carbon atom(s) or p-guanidinophenyl group, a group of the formula: —CO—R⁴⁶ wherein R⁴⁶ represents an alkyl group of up to 4 carbon atom(s),
a group of the formula: —O—Z⁴³—COOR⁴⁵⁰ wherein Z⁴³ represents an alkylene group of up to 6 carbon atom(s).
R⁴⁵⁰ represents a hydrogen atom, an alkyl group of up to 8 or p-guanidinophenyl group,
a group of the formula:

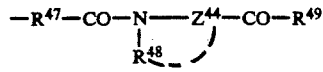

wherein

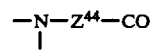

represents an amino acid residue, R⁴⁸ represents hydrogen atom or alkyl group of up to 4 carbon atom(s), and R⁴⁹ represents hydroxy group, alkoxy group of up to 4 carbon atom(s), amino group, amino group substituted by one or two alkyl group of up to 4 carbon atom(s), carbamoylmethoxy or carbamoylmethoxy group substituted by one or two alkyl group of up to 4 carbon atoms at nitrogen atom of carbamoyl group, R⁴⁷ represents single-bond or alkyl group of up to 4 carbon atom(s), or wherein

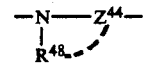

represents heterocyclic ring containing 3 to 6 carbon atoms and R⁴⁷ and R⁴⁹ has each same meaning as described hereinbefore,
(ii) R¹, R² and nitrogen atom bonded to R¹ and R₂ together represents heterocyclic ring containing at least one nitrogen atom(s) and substituted by —COOH, or unsubstituted heterocyclic ring containing at least one nitrogen atom(s),
R³ represents
(1) hydrogen atom,
(2) hydroxy atom,
(3) an alkyl group of up to 6 carbon atom(s),
(4) halogen atom,
(5) an alkoxy group of up to 4 carbon atom(s) or
(6) an acyloxy group of 2 to 5 carbon atoms,
m represents an integer of up to 4,
or non-toxic salts or acid addition salts thereof or process for the preparation thereof, or inhibitory agents of elastase containing them as active ingredient.

In this specification and claims, the term "alkyl group", "alkylene group", "alkenylene group", "alkoxy group" and "acyloxy group" means the straight- or branched- chained alkyl group, alkylene group, alkenylene group, alkoxy group and acyloxy group.

In the general formula (I), sulfonyl and carbonyl group represented by Y are preferred.

In the general formula (I), as an alkyl group of up to 6 carbon atom(s) represented by R³, methyl, ethyl, propyl, butyl, pentyl and hexyl group and the isomer thereof are cited, and all of them are preferred.

In the general formula (I), examples of the halogen atom, represented by $R^3$ and $R^4$ are, a fluorine atom, a chlorine atom, a bromine atom and an iodine.

In the general formula (I), examples of an alkoxy group of up to 4 carbon atom(s) represented by $R^3$, include methoxy, ethoxy, propoxy and butyloxy group and the isomer thereof, and all of them are preferred.

In the general formula (I), examples of an acyloxy group of 2 to 5 carbon atom(s) represented by $R^3$, include acetoxy, propionyloxy, butyryloxy and valeryloxy group and the isomer thereof are cited, and all of them are preferred.

In the general formula (I), examples of an alkyl group of up to 16 carbon atom(s) represented by $R^1$ and $R^2$, include methyl, ethyl, propyl, butyl, pentyl, hexyl, heptyl, octyl, nonyl, decyl, undecyl, dodecyl, tridecyl, tetradecyl, pentadecyl and hexadecyl group and the isomer thereof, and all of them are preferred.

In the general formula (I), examples of an alkylene group of up to 4 carbon atom(s) represented by X and $Z^{41}$, include methylene, ethylene, trimethylene and tetramethylene group and the isomer thereof, and all of them are preferred.

In the general formula (I), carbocyclic ring represented by 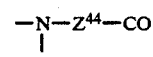 means mono- or bi-aromatic carbocyclic ring(s) containing not more than 12 carbon atoms which may be partially or fully saturated rings thereof.

Examples of these rings mentioned above are benzene, naphthalene, indene, azulene rings and partially or fully saturated rings thereof.

In the general formula (I), heterocyclic ring represented by 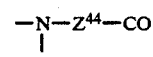 means mono-, bi-aromatic heterocyclic ring(s) containing not more than 12 carbon and hetero atoms which may be partially or fully saturated rings thereof. In above heterocyclic rings, rings containing one or two of hetero atom(s) are preferred.

Examples of these rings mentioned above are furan, thiophene, pyrrole, oxazole, isoxazole, thiazole, isothiazole, imidazole, pyrazole, furazane, pyran, pyridine, pyridazine, pyrimidine, pyrazine, indole, isoindole, benzofuran, benzothiophen, indolidine, chromen, quinoline, isoquinoline, quinolidine, purine, indazole, quinazoline, cinnoline, quinoxaline, phthalazin, pteridine rings and partially or fully saturated rings thereof.

In the general formula (I), examples of an alkyl group of up to 8 carbon atom(s) represented by $R^4$, include methyl, ethyl, propyl, butyl, pentyl, hexyl, heptyl and octyl and the isomer thereof are cited, and all of them are preferred.

In the general formula (I), examples of an alkoxy group of up to 14 carbon atom(s) represented by $R^4$, include methoxy, ethoxy, propoxy, butoxy, pentyloxy, hexyloxy, heptyloxy, octyloxy, nonyloxy, decyloxy, undecyloxy, dodecyloxy, tridecyloxy and tetradecyloxy group and the isomer thereof, and all of them are preferred, but particularly preferred are methoxy, pentyloxy, decyloxy and the isomer thereof.

In the general formula (I), examples of an alkylthio group of up to 6 carbon atom(s) represented by $R^4$, include methylthio, ethylthio, propylthio, butylthio, pentylthio and hexylthio group and the isomer thereof, and all of them are preferred.

In the general formula (I), as $R^4$, halogen, trihalomethyl, nitro, hydroxy, tetrazole, sulfonic acid and hydroxymethyl are particularly preferred.

In the general formula (I), examples of an alkyl group of up to 4 carbon atom(s) represented by $R^{41}$, $R^{42}$, $R^{43}$ and $R^{46}$, include methyl, ethyl, propyl and butyl group and the isomer thereof, and all of them are preferred.

In the general formula (I), examples of an alkenylene group of 2 to 4 carbon atom(s) represented by $Z^{41}$, include vinylene, propenylene and butenylene group and the isomer thereof, and all of them are preferred.

In the general formula (I), examples of an alkyl group of up to 8 carbon atom(s) represented by $R^{45}$, include methyl, ethyl, propyl, butyl, pentyl, hexyl, heptyl and octyl group and the isomer thereof, and all of them are preferred.

In the general formula (I), examples of an alkylene group of up to 6 carbon atom(s) represented by $Z^{43}$, include methylene, ethylene, trimethylene, tetramethylene, pentamethylene and hexamethylene group and the isomer thereof, and all of them are preferred.

In the general formula (I), an amino acid-residue represented by formula:

$$-\underset{|}{N}-Z^{44}-CO$$

represents every amino acid-residue, and these residues contain that carboxy group was converted into ester.

Preferable amino acid-residue is neutral, acidic or basic amino acid-residue. Examples of the residues mentioned above include glycine, alanine, β-alanine, valine, phenylalanine, lysine, methionine, tyrosine, proline, leucine, tryptophan, 4-amino butyric acid, 6-aminocaproic acid, 1-amino-1-phenylacetic acid, 2-amino-2-phenylpropionic acid, m-aminobenzoic acid, p-aminobenzoic acid.

Examples of an alkyl group of up to 4 carbon atom(s) represented by $R^{48}$, include methyl, ethyl, propyl and butyl group and the isomer thereof. Included as exemplary of an alkyl, in alkoxy group represented by $R^{49}$, in substituent of amino group and in substituent of carbamoylmethoxy group, methyl, ethyl, propyl and butyl group and the isomer thereof. Exemplary of the heterocyclic ring represented by

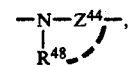

are azetidine, pyrrolidine, piperidine and perhydroazepine.

In the general formula (I), the heterocyclic ring represented by $R^1$, $R^2$ and the nitrogen atom bonded to $R^1$ and $R^2$ together, means a mono- heterocyclic ring containing 3 to 6 carbon atoms and 1 or 2 of nitrogen and/or oxygen atom(s).

Examples of these rings mentioned above are pyrrole, imidazole, pyrazole, pyrroline, pyrrolidine, imidazoline, imidazolidine, pyrazoline, pyrazolidine, piperidine, piperazine, morpholine, azetidine.

An acid addition salts of the compound of the general formula (I) are preferred non-toxic and water-soluble salts.

Suitable acid addition salts include, for example, an inorganic acid addition salt such as hydrochloride, hydrobromide, hydroiodide, sulfate, phosphate, nitrate, or an organic acid addition salt such as acetate, lactate, tartrate, benzoate, citrate, methanesulfonate, ethanesulfonate, benzenesulfonate, toluenesulfonate, isethionate, glucuronate, gluconate.

The compounds of the present invention of the general formula (I) may be converted into the corresponding salts by known methods. Non-toxic and water-soluble salts are preferable. Suitable salts, for example, are as follows: salts of alkaline metal (sodium, potassium etc.), salts of alkaline earth metal (carcium, magnesium etc.), ammonium salts, salts of pharmaceutically acceptable organic amine (tetramethylammonium, triethylamine, methylamine, dimethylamine, cyclopentylamine, benzylamine, phenethylamine, piperidineamine, monoethanolamine, diethanolamine, tris (hydroxymethyl)amine, lysine, arginine, N-methyl-D-glucamine etc.)

PROCESS FOR THE PREPARATION

According to the present invention, the compounds of the present invention of the general formula (I) may be prepared by any step described hereinafter.

In each formula, $R^{11}$ and $R^{21}$ have same meaning as that of $R^1$ and $R^2$, respectively provided that at least either $R^{11}$ or $R^{21}$ represents benzyloxycarbonyl group, $R^{12}$ and $R^{22}$ have same meaning as that of $R^1$ and $R^2$, respectively provided that at least either $R^{12}$ or $R^{22}$ represents carboxyl group, $R^{13}$ has same meaning that of $R^1$ or $R^2$ other than hydrogen atom, $R^{14}$ represents an alkyl group of up to 4 carbon atom(s), X represents halogen atom, $R^{31}$ represents an acyloxy group.

Step 1:

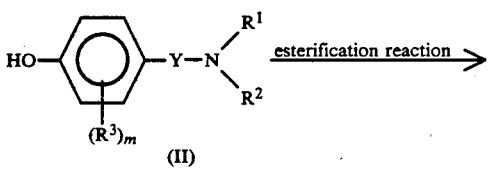

Step 2:

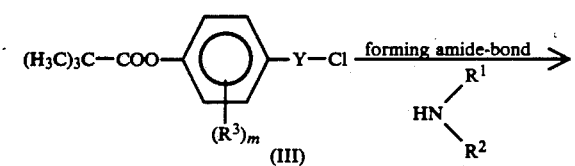

Step 3:

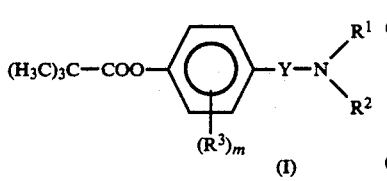

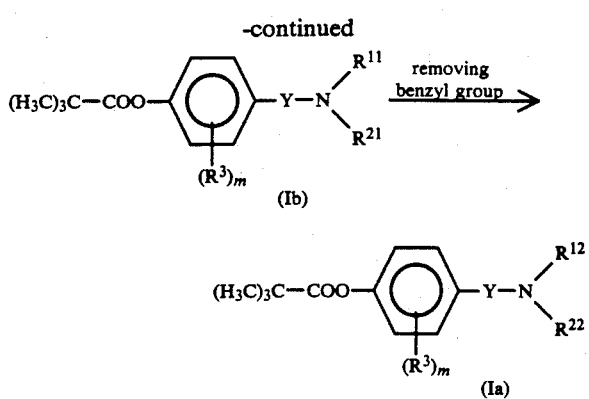

Step 4:

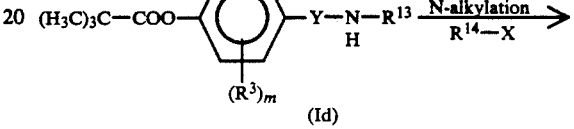

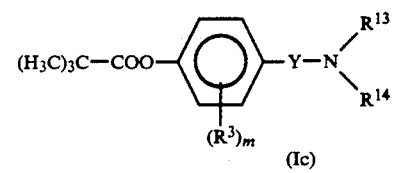

Step 5:

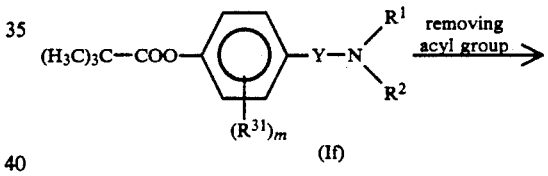

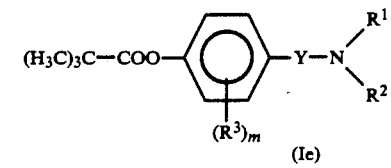

Step 1, which is an esterification reaction, conducted in the presence of a dehydrohalogenation agent in inert organic solvents (for example, methylene chloride, ethyl acetate, benzene, hexane, diethylether), may be carried out by reacting with corresponding pivaloyl halide under room temperature.

As for the dehydrohalogenation agent, there can be used a tertiary organic amine, or if desired, there can be used a inorganic base such as a metal bicarbonate, etc.

As a tertiary organic amine, there can be used aliphatic, aromatic or heterocyclic amine, for example, triethylamine, tributylamine, dimethylaniline, pyridine and the like.

Particularly, pyridine is preferable because it is useful also as a solvent of reaction ingredient.

Step 2, which is reaction forming the amide-bond, may be carried out by reacting the compound of the general formula (III) with corresponding amine in inert organic solvent (for example methylene chloride), in the presence of organic or inorganic base (for example, tertiary amine such as triethylamine), at a temperature of −20° C.~0° C. (preferably under cooling with ice).

Step 3, which is reaction for removing a benzyl group, may be carried out under an atmosphere of hydrogen gas, using palladium-carbon as catalyst in a mixture of inert organic solvent (for example acetic acid, THF), at a temperature of 0° C. to 40° C.

Step 4, which is N-alkylation reaction, may be carried out reacting with alkyl halide in suitable inert organic solvent (for example, benzene, tetrahydrofuran, dimethylformamide), in the presence of a suitable base (for example, sodium hydride), at from about room temperature to reflux temperature.

Step 5, which is reaction for eliminating the acyl group, may be carried out for example, in methanol, in the presence of a catalyst (for example, triethylamine), at or about room temperature.

The compounds of the general formula (II) and (III) used in the step hereinbefore may be prepared by combining known methods, for example according to scheme A hereinafter.

In the formula, G represents methoxy group or acetoxy group, and the other symbols have same meaning as described hereinbefore.

chromatography, thin layer chromatography or column chromatography using silica gel or magnesium silicate, washing or recrystallization. Purification may be carried out after each reaction, or after a series of reactions.

STARTING MATERIALS

The starting materials of formula (IV), (V) and (VII) in Scheme A are known compounds, or may be easily prepared by known methods.

For example, when $R^1$ and $R^2$ in the formula (IV) each represents $R^1$ and (3)- 16 of $R^2$ in the formula (I) mentioned above, those may be prepared according to scheme B described hereinafter.

In the formula, the sum of p and r represents an integer of 1 to 5, and r does not represent zero.

$R^{24}$ has same meaning that of $R^4$ other than (3) -16.

Scheme B

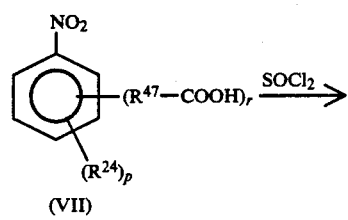

Scheme A

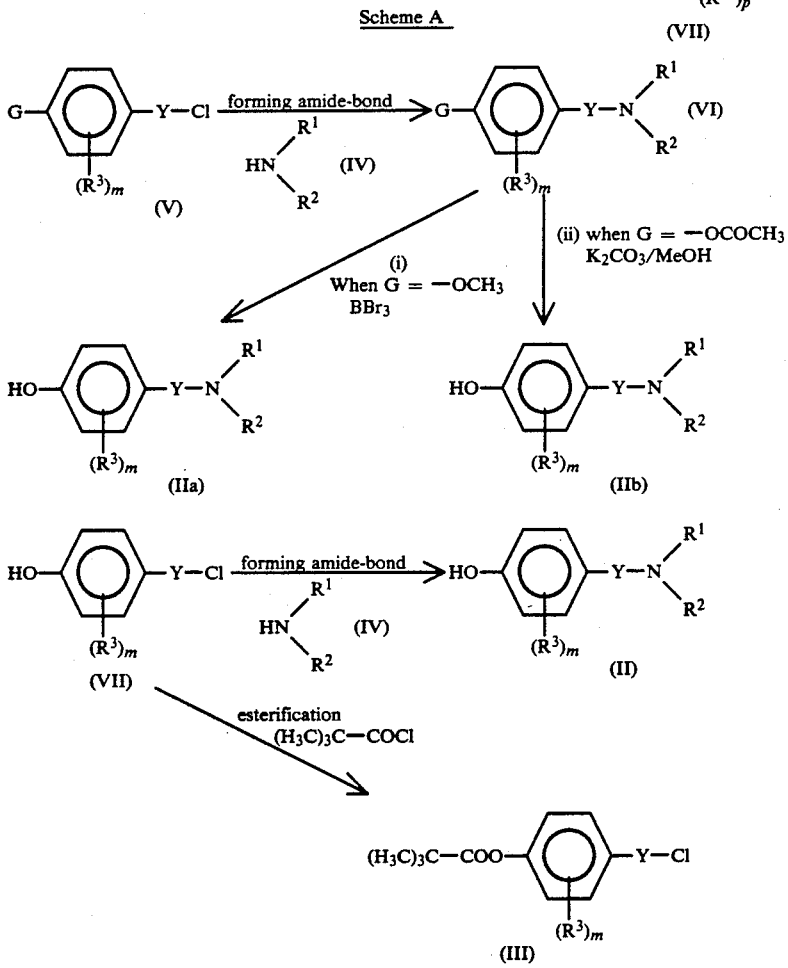

All reactions in the above schemes may be carried out by known methods.

In each reaction in the present specification, products may be purified by conventional manner. For example, purification may be carried out by distillation at atmospheric or reduced pressure, high performance liquid -continued
Scheme B

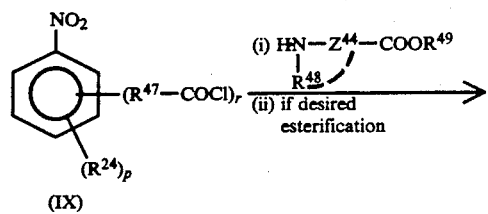

(IX)

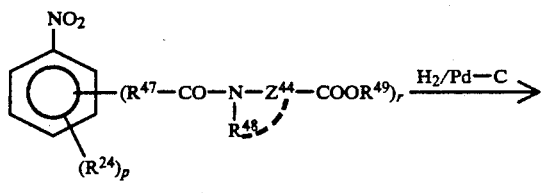

(X)

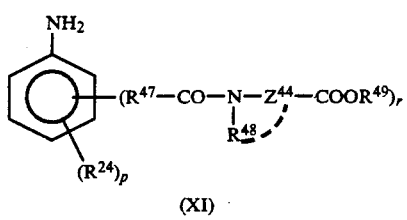

(XI)

EFFECT

Derivatives of p-substituted phenyl ester of pivalic acid of the general formula (I) of the present invention, and non-toxic acid and acid addition salts thereof, have an inhibitory effect on elastase.

Accordingly, the derivatives of the present invention are useful for treatment and/or prevention of diseases induced by the abnormal enhancing of the degradation of elastin, collagen fiber and/or proteoglican, by the action of elastase, in mammals, especially in human beings.

Examples of such diseases are pulmonary emphysema, atherosclerosis, rheumatoid arthritis and the like.

The inhibitory effects of the compounds of the invention on elastase were confirmed by the screening system disclosed below.

INHIBITORY EFFECT ON ELASTASE (1) Method of experiment

The test was carried out by a slight modification of the method of Bieth et al [see Biochem. Med., 75, 350 (1974)] using elastase from human neutrophil.

Namely, it is a spectrophotometric method using the synthesized substrate [succinyl-alanyl-prolyl-alanyl-p-nitroanilide (Suc-Ala-Pro-Ala-pNA, produced by peptide laboratory)] which has comparatively high specificity on neutrophil elastase.

The reaction mixture consisted of 1 mM Suc-Ala-Pro-Ala-pNA (dissolving in N-methylpyrrolidone to the concentration of 100 mM, and then adding 1/100 amount of the solution to the reaction mixture.), 0.1 M buffer solution of tris-hydrochloric acid (pH 8.0), 0.2 M sodium chloride aqueous solution, the sample solution of various concentrations and enzyme solution in a final volume of 1.0 ml was incubated at 37° C. for 30 minutes.

The reaction was stopped by the addition of 100 μl of 50% acetic acid into the reaction mixture, and then p-nitro anilide released was measured on absorbance of 405 nm.

Inhibition percentage of the test compounds was calculated by the following equation:

$$\text{Inhibition \%} = \left(1 - \frac{OD_{450} \text{ nm count of sample} - \text{background}}{OD_{405} \text{ nm count of control} - \text{background}}\right) \times 100$$

TABLE I

Inhibitory effect of elastase

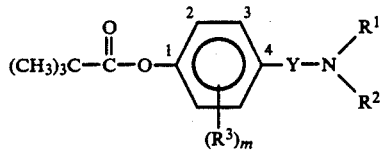

| Example No. | Structure | Name | Inhibitory effect of elastase (μM) |
|---|---|---|---|
| 1 | (phenyl-SO₂N(CH₃)-phenyl-Br) | p-[N-(p-bromophenyl)-N-methylsulfamoyl] phenyl ester of pivalic acid | 0.031 |
| 1(2) | (phenyl-SO₂NH₂) | p-sulfamoylphenyl ester of pivalic acid | 0.77 |

TABLE I-continued

Inhibitory effect of elastase $$(CH_3)_3C-\overset{O}{\underset{\|}{C}}-O-\underset{(R^3)_m}{\overset{2\quad 3}{\underset{1\quad 4}{\bigcirc}}}-Y-N\overset{R^1}{\underset{R^2}{\big\langle}}$$

| No. | Structure | Name | Value |
|---|---|---|---|
| 1(3) | –⟨⟩–SO$_2$NH–⟨⟩–H (cyclohexyl) | p-(N-cyclohexylsulfamoyl)phenyl ester of pivalic acid | 0.042 |
| 1(8) | –⟨⟩–SO$_2$NH–⟨⟩–Cl | p-[N-(p-chlorophenyl)sulfamoyl]phenyl ester of pivalic acid | 0.03 |
| 1(12) | –⟨⟩–SO$_2$N(imidazolyl) | p-[(1-imidazoyl)sulfonyl]phenyl ester of pivalic acid | 0.05 |
| 1(14) | –⟨⟩–SO$_2$NH–(2-pyridyl) | p-[N-(α-pyridyl)sulfamoyl]phenyl ester of pivalic acid | 0.19 |
| 1(15) | –⟨⟩–SO$_2$N(Ar)(SO$_2$Ar') where Ar = p-OCCH$_3$-phenyl, Ar' = p-OCC(CH$_3$)$_3$-phenyl | 1-acetoxy-4-[N,N-bis(p-pivaloyloxy-phenylsulfonyl)amino]benzene | 0.048 |
| 2(5) | –⟨⟩–SO$_2$NH–C(CH$_3$)$_3$ | p-(N-tert-butylsulfamoyl)phenyl ester of pivalic acid | 0.053 |
| 2(38) | CH$_3$–⟨⟩–SO$_2$NH–⟨⟩–COOCH$_2$CON(C$_2$H$_5$)$_2$ | 2-methyl-4-[N-(N,N-diethylcarbamoylmethoxycarbonyl)phenyl)sulfamoyl]phenyl ester of pivalic acid | 0.072 |
| 2(49) | CH$_3$–⟨⟩–SO$_2$NH–⟨⟩–(1,4-dioxa-2-COOH) | 2-methyl-4-[N-(1,4-dioxa-2-carboxy-8-yl-naphthalene)sulfamoyl]phenyl ester of pivalic acid | 0.15 |
| 2(51) | CH$_3$–⟨⟩–SO$_2$NH–⟨⟩–O–(CH$_2$)$_3$–COOH | 2-methyl-4-[N-(o-carboxypropoxyphenyl)sulfamoyl]phenyl ester of pivalic acid | 0.64 |

TABLE I-continued

Inhibitory effect of elastase

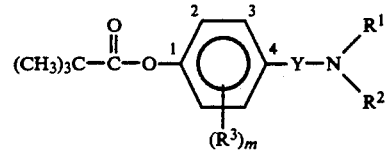

| Example No. | Structure | Name | Inhibitory effect of elatase (μM) |
|---|---|---|---|
| 2(62) | CH₃–⟨⟩–SO₂NH–⟨⟩–CON(pyrrolidine-COOH) | 2-methyl-4-[N-(o-carbonylphenyl)sulfamoyl]phenyl ester of pivalic acid | 0.69 |
| 2(63) | –⟨⟩–SO₂NH–⟨⟩–CONHCH₂COOH | N-[O-(p-pivaloyloxybenzene)sulfonylaminobenzoyl]glycine | 0.044 |

Structure

| Example No. | Structure | Name | Inhibitory effect of elatase (μM) |
|---|---|---|---|
| 2(67) | CH₃–⟨⟩–SO₂NH–⟨⟩–CONH–CH(CH₂Ph)COOH | N-[O-(3-methyl-4-pivaloyloxybenzene)sulfonylaminobenzyoyl-L-phenylanine | 0.41 |
| 2(68) | CH₃–⟨⟩–SO₂NH–⟨⟩–CONH–CH((CH₂)₂SCH₃)–COOH | N-[O-(3-methyl-4-pivaloyloxybenzene)sulfonylaminobenzoyl]-dl-methionine | 0.20 |
| 2(69) | CH₃–⟨⟩–SO₂NH–⟨⟩–CONH–CH((CH₂)₄NH₂)–COOH·HCl | N-[O-(3-methyl-4-pivaloyloxybenzene)sulfonylaminobenzoyl]-L-lisine hydrochloride | 0.52 |
| 2(80) | –⟨⟩–SO₂NH–⟨⟩(SCH₃)–CONHCH₂COOH | N-[5-methylthio-2-(p-pivaloyloxybenzene)sulfonylaminobenzoyl]glycine | 0.021 |
| 2(87) | –⟨⟩–SO₂NH–⟨⟩(S(CH₂)₂CH₃)–CONHCH₂COOH | N-[2-(p-pivaloyloxybenzene)sulfonylamino-5-propylthiobenzoyl]glycine | 0.024 |
| 4(5) | –⟨⟩–SO₂NH–(CH₂)₂–⟨⟩ | p-(N-phenethylsulfamoyl)phenyl ester of pivalic acid | 0.072 |

TABLE I-continued

Inhibitory effect of elastase $(CH_3)_3C-\overset{\overset{O}{\|}}{C}-O-\underset{(R^3)_m}{\overset{2\quad 3}{\underset{1\quad\phantom{0}\quad 4}{\bigcirc}}}-Y-N\overset{R^1}{\underset{R^2}{\diagdown}}$

| 5(3) | -◯-SO₂NH-◯-COOH | p-[N-(o-carboxyphenyl)sulfamoyl]phenyl ester of pivalic acid | 0.023 |

The result of the experiment showed that the compounds of the present invention have an inhibitory effect on elastase.

TOXICITY

Further, it was confirmed that the toxicity of the compounds of the present invention is low enough such that they can be used safely for medical supplies.

APPLICATION

Accordingly, it was confirmed that the compounds of the present invention can be useful for the treatment and/or prevention of diseases induced by abnormal enhancing of degradation of proteins such as elastin and the like, by the action of elastase in mammals, especially in human beings.

ADMINISTRATION

For the purpose mentioned above, the compounds of the present invention, described in the general formula (I) or an acid addition salts thereof may normally be administered systemically or partially, usually by oral or parenteral administration.

The dose to be administered is determined depending upon age, body weight, symptom, the desired therapeutic effect, the route of administration, and the duration of the treatment etc. In the human adult, the doses per person for one time are generally between 1 mg and 500 mg, by oral administration up to several times per day, and between 0.1 mg and 200 mg, by parenteral administration (preferably by intravenous administration) up to several times per day.

As mentioned above, the doses to be used depend on various conditions. Therefore, there are cases in which doses lower than the ranges specified above and doses greater than the ranges specified above, may be used.

Solid compositions according to the present invention for oral administration include compressed tablets, dispersible powders and granules. In such solid compositions, one or more of the active compound(s) is, or are, admixed with at least one inert diluent such as lactose, mannitol, glucose, hydroxypropyl cellulose, microcrystalline cellulose, starch, polyvinyl-pyrrolidone or magnesium metasilicate aluminate. The compositions may also comprise, as is normal practice, additional substances other than inert diluents e.g. lubricating agents such as magnesium stearate, and, disintegrating agents such as cellulose calcium glycolate, stabilizing agents such as lactose, and solubilizers such as glutamic acid and asparaginic acid. The tablets or pills may, if desired, be made into gastric film-coated or enteric film-coated tablets or pills, such as sugar-coated, gelatin-coated, hydroxypropylcellulose-coated or hydroxypropylmethylcellulose phthalate-coated tablets or pills; two or more layers may be used. The compositions for oral administration also include capsules of absorbable material such as gelatin.

Liquid compositions for oral administration include pharmaceutically-acceptable emulsions, solutions, suspensions, syrups and elixirs containing inert diluents commonly used in the art such as distilled water or ethanol. Besides inert diluents such compositions may also comprise adjuvants such as wetting and suspending agents, and sweetening, flavouring, perfuming and preserving agents.

Other compositions for oral administration include spray compositions which may be prepared by known methods and which comprise one or more of the active compound(s). Besides inert diluents such compositions may also comprise stabilizers such as sodium bisulfite and buffer for isotonicity, for example sodium chloride, sodium citrate or citric acid.

The manufacturing methods of spray compositions have been described in detail, for example, in the specifications of U.S. Pat. Nos. 2,868,691 and 3,095,355.

Preparations for injection according to the present invention for parenteral administration include sterile aqueous or non-aqueous solutions, suspensions or emulsions. Example of aqueous solvents or suspending media are distilled water for injection and physiological salt solution. Examples of non-aqueous solvents or suspending media are propylene glycol, polyethylene glycol, vegetable oils such as olive oil, alcohols such as ethanol, Polysorbate 80 (registered Trade Mark). These compositions may also include adjuvants such as preserving, wetting, emulsifying and dispersing agents stabilizing agents (e.g. lactose) and solubilizers (e.g. glutamic acid and asparaginic acid). They may be sterilized, for example, by filtration through a bacteria-retaining filter, by incorporation of sterilizing agents in the compositions or by irradiation. They may also be manufactured in the form of sterile solid compositions which can be dissolved in sterile water or some other sterile injectable medium immediately before use.

Other compositions for parenteral administration include liquids for external use, and endermic liniments such as ointments, suppositories for rectal administration and pessaries for vaginal administration which comprise one or more of the active compound(s) and may be prepared by known methods.

EXAMPLES AND COMPARATIVE EXAMPLES

The following Reference Examples and Examples illustrate the preparation of compounds of the present invention, however, the present invention is not restricted to them. In the Reference Examples and Examples, "TLC", "NMR" and "IR" each represents "thin layer chromatography", "nuclear magnetic resonance" and "infrared absorption spectrum", respectively.

The solvents in the parentheses show the developing or eluting solvents and the ratios of the solvents used are by volume in chromatographic separation.

Unless otherwise specified, "IR" were measured by KBr method, and "NMR" were measured in bichloroform (CDCl₃).

REFERENCE EXAMPLE 1

1-(N-methyl-N-phenyl)sulfamoyl-4-methoxybenzene

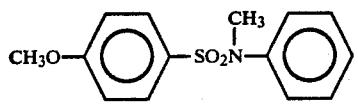

p-methoxybenzenesulfonyl chloride (965 mg) was dissolved in the mixture of triethylamine (2 ml), methylaniline (500 mg) and methylene chloride (10 ml) under cooling with ice, and the mixture was stirred for 30 minutes.

The reaction solution was stirred overnight at room temperature. After the reaction was finished, the reaction solution was extracted with ether. The extract was washed successively with 1N-HCl, water and a saturated aqueous solution of sodium chloride.

The solution was dried over sodium sulfate, and distilled off under reduced pressure to give the title compounds.

REFERENECE EXAMPLE 2 p-N-methyl-N-(p-bromophenyl)sulfamoyl]phenol

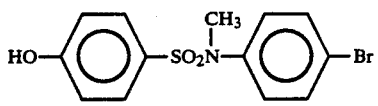

Boron tribromide (2.2 ml) was added to the solution of methylene chloride (10 ml) of the compound obtained by Reference Example 1 under cooling with ice, and stirred for 2 hours at room temperature.

The reaction solution was allowed to cool to −20° C. ~ −30° C., and water was added thereto, and the solution obtained was extracted with ethyl acetate. The extract was washed successively with water and saturated aqueous solution of sodium chloride.

The solution was dried over sodium sulfate, and distilled off under reduced pressure and the residue was purified by column chromatography on silica-gel (methylene chloride: ethyl acetate=10:1) to give the title compound (900 mg) having the following physical data;

TLC: Rf 0.20 (methylene chloride: ethyl acetate=30:1).

REFERENCE EXAMPLE 3 p-[N-(p-tolyl)carbamoyl]phenol

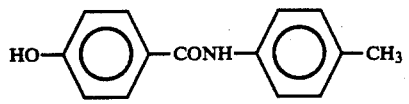

Potassium carbonate (500 mg) was added into methanol solution (50 ml) of [p-acetoxy-N-(p-tolyl)]benzamide (300 mg) obtained by the same procedure as Reference Example 1, and the mixture was stirred overnight.

The obtained reaction solution was distilled off under reduced pressure, and extracted with ethyl acetate. The extract was washed successively with 1N-hydroic acid, water and saturated aqueous solution of sodium chloride.

The solution was dried with magnesium sulfate, and distilled off under reduced pressure to give the title compound having the following physical data.

TLC Rf 0.31 (methylene chloride : ethyl acetate=10:1).

EXAMPLE 1 p-[N-(p-bromophenyl)-N-methylsulfamoyl]phenyl ester of pivalic acid

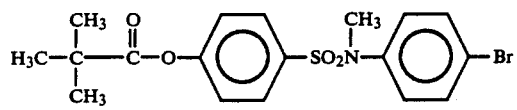

Pivaloyl chloride (0.5 ml) was added to the mixture solution of triethylamine (1.5 ml)-methylene chloride (5 ml) of the compounds obtained by procedure of Reference Example 2 under cooling with ice. The reaction solution was allowed to stand for 10 minutes, and stirred for one hour at room temperature.

The reaction solution was extracted with ether, and the extract was washed successively with water, 1N-HCl, water, saturated aqueous solution of sodium bicarbonate, water and saturated aqueous solution of sodium chloride. The solution was dried with sodium sulfate, and distilled off under reduced pressure.

The concentrate was recrystallized with ethyl acetate-hexane to give the title compound (510 mg) having the following physical data.

TLC: Rf 0.81 (methylene chloride : ethyl acetate=30:1);

IR: 1750, 1590, 1460, 1400, 1350 cm$^{-1}$.

Hereinafter, the title compound, which was described in the following Table II and III, was given by using corresponding starting materials and by operating the same procedure as Reference Example 1→Reference Example 2 (or Reference Example 3)→Example 1.

TABLE II $$(CH_3)_3C-\overset{O}{\underset{\|}{C}}-O-\underset{(R^3)_m}{\text{C}_6H_3}-SO_2N\overset{R^1}{\underset{R^2}{<}}$$

| Example No. | $-N\overset{R^1}{\underset{R^2}{<}}$ | Name | TLC | IR (cm$^{-1}$) or NMR |
|---|---|---|---|---|
| 1(1) | —NH—C$_6$H$_5$ | p-(N-phenylsulfamoyl)phenyl ester of pivalic acid | Rf 0.3 (hexane: ethyl acetate: = 5:2) | δ 7.7(2H,d), 7.3~6.9(7H,m), 6.5(1H,6s), 1.3(9H,s) |
| 1(2) | —NH$_2$ | p-sulfamoylphenyl ester of pivalic acid | Rf 0.72 (hexane: ethyl acetate: = 1:2) | ν 3400,3280,1720, 1580,1480,1350, 1200,1160,1120 |
| 1(3) | —NH—C$_6$H$_{11}$ | p-(N-cyclohexylsulfamoyl)phenyl ester of pivalic acid | Rf 0.82 (hexane: ethyl acetate: = 1:1) | ν 3280,2940,1750, 1590,1480,1440, 1320,1210,1160, 1100 |
| 1(4) | —NH—C$_6$H$_4$—CH$_3$ | p-[N-(p-tolyl)sulfamoyl]phenyl ester of pivalic acid | Rf 0.62 (methylene chloride: ethyl acetate: = 30:1) | ν 3300,1740,1580, 1500,1380,1330, 1270,1200 |
| 1(5) | —NH—C$_6$H$_4$—CO$_2$CH$_2$—C$_6$H$_5$ | p-[N-(p-benzyloxycarbonylphenyl) sulfamoyl]phenyl ester of pivalic acid | Rf 0.75 (hexane: ethyl acetate: = 1:1) | ν 1750,1720,1600, 1460,1340,1270, 1150,1100 |
| 1(6) | —NH—C$_6$H$_4$—N(CH$_3$)$_2$ | p-[N-(4-N,N-dimethylamino)phenyl) sulfamoyl]phenyl ester of pivalic acid | Rf 0.78 (hexane: ethyl acetate: = 1:2) | ν 1750,1610,1590, 1520,1330,1200, 1150,1100 |
| 1(7) | —NH—C$_{10}$H$_{21}$ | p-(N-decylsulfamoyl)phenyl ester of pivalic acid | Rf 0.60 (methylene chloride: ethyl acetate: = 30:1) | ν 3300,2930,2850, 1750,1590 |
| 1(8) | —NH—C$_6$H$_4$—Cl | p-[N-(4-chlorophenyl)sulfamoyl] phenyl ester of pivalic acid | Rf 0.52 (methylene chloride: ethyl acetate: = 30:1) | ν 3260,2970,1750, 1590,1490,1450, 1340 |
| 1(9) | —NH—C$_6$H$_4$—Cl (meta) | p-[N-(m-chlorophenyl)sulfamoyl] phenyl ester of pivalic acid | Rf 0.50 (methylene chloride: ethyl acetate: = 30:1) | ν 3250,1750,1590, 1480,1400,1330, 1200 |
| 1(10) | —NH—(β-pyridyl) | p-[N-(β-pyridyl)sulfamoyl]phenyl ester of pivalic acid | Rf 0.50 (methylene chloride: methanol = 10:1) | ν 3600~3200,1750, 1580,1470,1400 13500,1310,1260, 1200 |
| 1(11) | —NH—C$_6$H$_4$—C$_5$H$_{11}$ | p-[N-(p-pentylphenyl)sulfamoyl] phenyl ester of pivalic acid | Rf 0.46 methylene chloride: ethyl acetate: = 30:1) | ν 3960,3920,3850, 3250,1750,1610, 1590,1510,1480, 1460,1400,1330, (neat) |

TABLE II-continued

Structure:
$(CH_3)_3C-\overset{O}{\underset{\|}{C}}-O-\langle\text{phenyl}(R^3)_m\rangle-SO_2N\langle{}^{R^1}_{R^2}\rangle$

| Example No. | $-N\langle{}^{R^1}_{R^2}\rangle$ | Name | TLC | IR (cm$^{-1}$) or NMR |
|---|---|---|---|---|
| 1(12) | −N(imidazolyl) | p-[(1-imidazolyl)sulfonyl]phenyl ester of pivalic acid | Rf 0.52 (methylene chloride: ethyl acetate = 5:1) | δ 7.96(2H,d),8.0 (1H,m),7.28(2H,d),7.28(1H,m), 7.09(1H,m),1.36 (9H,s) |
| 1(13) | −N(morpholino) | (p-morpholinosulfonyl)phenyl ester of pivalic acid | Rf 0.19 (methylene chloride: ethyl acetate = 30:1) | ν 2970,2860,1759, 1590,1480,1340 |
| 1(14) | −NH-(α-pyridyl) | p-[N-(α-pyridyl)sulfamoyl]phenyl ester of pivalic acid | Rf 0.64 (chloroform: methanol: = 30:1) | ν 3200~2300,1750, 1630,1610,1520, 1490,1480,1460, 1380,1360 |
| 1(15) | complex bis-structure | 1-methoxy-4-[N,N-bis(p-pivaloyloxyphenylsulfonyl)amino]benzene | Rf 0.61 (methylene chloride: ethyl acetate = 30:1) | ν 3400,2970,1750, 1590,1480 |

TABLE III

Structure:
$(CH_3)_3C-\overset{O}{\underset{\|}{C}}-O-\langle\text{phenyl}(R^3)_m\rangle-CON\langle{}^{R^1}_{R^2}\rangle$

| Example No. | $-N\langle{}^{R^1}_{R^2}\rangle$ | Name | TLC | IR (cm$^{-1}$) or NMR |
|---|---|---|---|---|
| 1(16) | −NH−⟨p-tolyl⟩−CH$_3$ | p-[N-(p-tolyl)carbamoyl]phenyl ester of pivalic acid | Rf 0.46 (methylene chloride: ethyl chloride: = 30:1) | ν 3300,2960,1740, 1640,1600,1500 |

REFERENCE EXAMPLE 4 sodium salt of p-pivaloyloxybenzenesulfonic acid

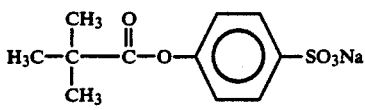

Pivaloyl chloride (2.4 g) was dissolved in the mixture of 4N-aqueous solution of sodium hydroxide (7.5 ml) of phenol 4-sulfonic acid (1.74 g) and tetrahydrofuran (5 ml), and the mixture was stirred for 10 minutes under cooling with ice. The mixture was reacted for one hour at room temperature.

The reaction solution was distilled off under reduced pressure, and the crystal was filtered off.

The obtained crystal was washed twice with a small amount of ice-water, and dried to give the title compound (1.26 g) having the following physical data.

TLC : Rf 0.65 (ethyl acetate : acetic acid : water =6:2:1).

REFERENCE EXAMPLE 5 p-pivaloyloxybenzenesulfonyl chloride

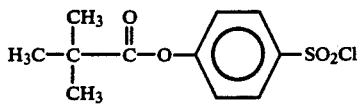

Thionyl chloride (2.1 ml) was added to dimethylformamide solution (33 ml) of the compound (2.8 g) of Reference Example 4, and the mixture was stirred for 30 minutes under cooling with ice, and stirred for 30 minutes at room temperature.

The reaction solution was extracted with ether-hexane (1:1), and the extract was washed twice with ice-water.

The solution was dried with magnesium sulfate to give the title compound (2.49 g) having the following physical data.

TLC Rf 0.34 (hexane : ethyl acetate = 10 : 1).

EXAMPLE 2 p-[N-((trans-p-carboxycyclohexyl)methyl)sulfamoyl]-phenyl ester of pivalic acid

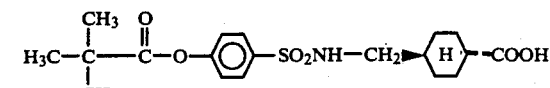

By using sulfonyl chloride of Reference Example 5, and by the same procedure of Reference Example 1, the title compound (110 mg) having the following physical data was obtained.

TLC : Rf 0.32 (chloroform : methanol : acetic acid=100:5:1);

NMR 7.9(2H,d), 7.25(2H,d), 4.4(1H,m), 2.8(2H,m), 2.4–1.0(9H,m), 1.35(9H,s).

Hereinafter, by using sulfonyl chloride of Reference Example 5 and corresponding amine, and by the same procedure of Example 2, the desired compounds described in the following Table IV and V were obtained.

TABLE IV $$(CH_3)_3C-\underset{\underset{O}{\|}}{C}-O-\underset{\underset{(R^3)_m}{}}{\overset{\overset{SO_2-N\underset{R^2}{\overset{R^1}{}}}{}}{C_6H_4}}$$

| Example No. | $-N\begin{smallmatrix}R^1\\R^{3*}\end{smallmatrix}R^2$ | Name | TLC | IR (cm$^{-1}$) or NMR |
|---|---|---|---|---|
| 2(1) | $-NH-$(C$_6$H$_4$)$-$CH$_2$COOH / $-$H | p-[N-(p-carboxymethylphenyl)sulfamoyl]phenyl ester of pivalic acid | Rf 0.3 (chloroform: methanol: acetic acid = 100:5:1) | (CDCl$_3$ + CD$_3$OD): δ 7.8(2H,d), 7.4~7.0(6H,m), 3.55(2H,s), 1.35(9H,s) |
| 2(2) | $-NH-$(C$_6$H$_4$)$-$CH=CH$-$COOH / $-$H | p-[N-(p-trans-2-carboxyvinyl)phenyl)sulfamoyl]phenyl ester of pivalic acid | Rf 0.33 (chloroform: methanol: acetic acid = 100:5:1) | (CDCl$_3$ + CD$_3$OD): δ 8.0~7.0(10H,m), 6.2(1H,d), 1.35(9H,s) |
| 2(3) | $-NH-$(C$_6$H$_4$)$-$COOH (m) / $-$H | p-[N-(m-carboxyphenyl)sulfamoyl]phenyl ester of pivalic acid | Rf 0.31 (chloroform: methanol: acetic acid = 100:5:1) | (CDCl$_3$ + CD$_3$OD): δ 7.85(2H,d), 7.8~7.65(2H,m), 7.5~7.3(3H,m), 7.2~7.0(2H,d) |
| 2(4) | $-NH-$CH$_2-$(C$_6$H$_4$)$-$COOH / $-$H | p-[N-(p-carboxybenzyl)sulfamoyl]phenyl ester of pivalic acid | Rf 0.31 (chloroform: methanol: acetic acid = 100:5:1) | δ 8.1~7.8(4H,m), 7.5~7.2(5H,m), 4.2(2H,s), 1.35(9H,s) |
| 2(5) | $-NH-C(CH_3)_3$ / $-$H | p-(N-tert-butylsulfamoyl)phenyl ester of pivalic acid | Rf 0.65 (methylene chloride: ethyl acetate = 30:1) | ν 3260,2980,1740, 1590,1480,1310, 1200 |

TABLE IV-continued

| | | | |
|---|---|---|---|
| 2(6) | 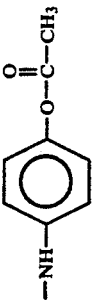<br>—H | p-[N-(p-acetoxyphenyl)sulfamoyl] phenyl ester of pivalic acid | Rf 0.58 (ethyl acetate: hexane = 1:1) | ν 3260,2960,1750, 1740,1590,1300, 1470,1400,1340, 1230,1190,1150, 1100 |
| 2(7) | 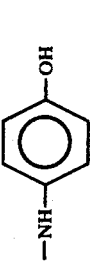<br>—H | p-[N-(p-hydroxyphenyl)sulfamoyl] phenyl ester of pivalic acid | Rf 0.08 (methylene chloride: ethyl acetate = 30:1) | ν 1745,1590,1510, 1400,1320,1270, 1200 |
| 2(8) | 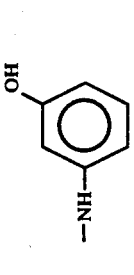<br>—H | p-[N-(m-hydroxyphenyl)sulfamoyl] phenyl ester of pivalic acid | Rf 0.10 (methylene chloride: ethyl acetate = 30:1) | ν 3400,3240,1640, 1610,1600,1480 |
| 2(9) | 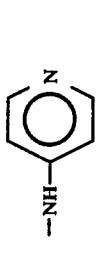<br>—H | p-[N-(4-pyridyl)sulfamoyl]phenyl ester of pivalic acid | Rf 0.30 (chloroform: methanol = 10:1) | ν 3500~2300,1750, 1630,1590,1490, 1350 |
| 2(10) | 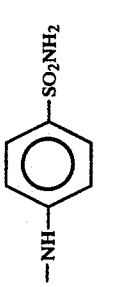<br>—H | p-[N-(p-sulfamoylphenyl)sulfamoyl] phenyl ester of pivalic acid | Rf 0.18 (chloroform: methanol: acetic acid = 100:5:1) | (CDCl$_3$ + CD$_3$OD): δ 7.9(2H,d),7.75 (2H,d),7.3(2H, d),7.2(2H,d), 1.35(9H,s) |
| 2(11) | 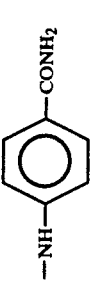<br>—H | p-[N-(p-carbamoylphenyl)sulfamoyl] phenyl ester of pivalic acid | Rf 0.22 (chloroform: methanol: acetic acid = 100:5:1) | (CDCl$_3$ + CD$_3$OD): δ 7.85(2H,d), 7.70(2H,d), 7.18(2H,d), 7.14(2H,d) |

TABLE IV-continued

| | Structure | R group | Name | Rf | Spectral data |
|---|---|---|---|---|---|
| 2(12) | —NH—CH₂—(2-pyridyl) | —H | p-[N-(α-pyridyl)methyl)sulfamoyl] phenyl ester of pivalic acid | Rf 0.75 (chloroform: methanol: =10:1) | ν 1750,1590,1480, 1330,1200,1160 |
| 2(13) | —NH—CH₂—(3-pyridyl) | —H | p-[N-(β-pyridyl)methyl)sulfamoyl] phenyl ester of pivalic acid | Rf 0.57 (chloroform: methanol: = 10:1) | ν 1750,1590,1480, 1320,1200,1150, 1100 |
| 2(14) | —NH—CH₂—(4-pyridyl) | —H | p-[N-(4-pyridyl)methyl)sulfamoyl] phenyl ester of pivalic acid | Rf 0.57 (chloroform: methanol: = 10:1) | ν 1750,1600,1590, 1480,1420,1320, 1200 |
| 2(15) | —NH—(o-hydroxyphenyl) | —H | p-[N-(o-hydroxyphenyl)sulfamoyl] phenyl ester of pivalic acid | Rf 0.42 (methylene chloride: ethyl acetate = 10:1) | ν 3450,3250,1730, 1590,1480,1430 |
| 2(16) | (3-carboxy)piperidinyl | —H | P-[(3-carboxy)piperidinosulfonyl] phenyl ester of pivalic acid | Rf 0.41 (chloroform: methanol: acetic acid = 100:5:1) | δ 7.8(2H,d), 7.3(2H,d), 4.0~3.43H,b), 3.0~1.3(6H,b), 1.35(9H,s) |
| 2(17) | —NH—phenyl | 2-CH₃ | 2-methyl-4-(N-phenylsulfamoyl) phenyl ester of acetic acid | Rf 0.44 (hexane: ethyl acetate = 5:2) | δ 7.7~7.5(2H,m), 7.4~7.0(6H,m), 6.45(1H,bs), 2.2(3H,s), 1.35(9H,s) |

TABLE IV-continued

| | | | |
|---|---|---|---|
| 2(18) | [structure: N-methyl aniline with CH₃ and COOH substituents], 2-CH₃ | 2-methyl-4-[N-methyl-N-(o-carboxy-1-sulfamoyl)]phenyl ester of pivalic acid | Rf 0.43 (chloroform: methanol: acetic acid = 100:5:1) | δ 7.9(1H,dd), 7.7~7.0(6H,m), 3.35(3H,s), 2.2(3H,s), 1.4(9H,s) |
| 2(19) | [structure: pyrrolidine with COOH], 2-CH₃ | 2-methyl-4-[(2S-carboxy-1-pyrrolidinyl)sulfonyl]phenyl ester of pivalic acid | Rf 0.26 (chloroform: methanol: acetic acid = 100:5:1) | δ 7.8(1H,s),7.75 (1H,d),7.2(1H, d),4.4~4.2(1H, m),2.4~1.6(7H, m),1.4(9H,m) |
| 2(20) | [structure: cyclohexane with NH-CH₂- and COOH], 2-CH₃ | 2-methyl-4-[N-(p-carboxycyclohexanemethyl)sulfamoyl] phenyl ester of pivalic acid | Rf 0.40 (chloroform: methanol: acetic acid = 100:5:1) | δ 7.8(1H,s), 7.75(1H,d), 2.85(2H,d), 2.3(3H,s), 1.4(9H,s) |
| 2(21) | [structure: piperidine with 4-COOH], 2-CH₃ | 2-methyl-4-[(4-carboxy) piperidinosulfonyl]phenyl ester of pivalic acid | Rf 0.36 (chloroform: methanol: acetic acid = 100:5:1) | δ 7.65(1H,s),7.6 (1H,d),3.8~3.4 (3H,b),2.7~2.3 (2H,m),2.25(3H, s),2.2~1.6(5H, b),1.4(9H,s) |
| 2(22) | [structure: piperidine with 3-COOH], 2-CH₃ | 2-methyl-4-[(3-carboxy) piperidinosulfonyl]phenyl ester of pivalic acid | Rf 0.36 (chloroform: methanol: acetic acid = 100:5:1) | δ 7.68(1H,s),7.61 1H,d),3.9~3.3 (2H,m),2.8~2.4 (3H,m),2.25(3H, s),1.35(9H,s) |

TABLE IV-continued

| | | | |
|---|---|---|---|
| 2(23) | ![structure: phenyl with COOCH3, -NH, 2-CH3] | 2-methyl-4-[(N-((o-methoxycarbonyl)phenyl)sulfamoyl]phenyl ester of pivalic acid | Rf 0.6 (methylene chloride: ethyl acetate = 30:1) | ν 3125,2970,1740, 1685,1600,1580, 1490,1265,1110, 940,760 |
| 2(24) | ![structure: phenyl with COCH3, -NH, 2-CH3] | 2-methyl-4-[N-((o-acetyl)phenyl) sulfamoyl]phenyl ester of pivalic acid | Rf 0.6 (methylene chloride: ethyl acetate = 30:1) | ν 2980,1755,1640, 1605,1580,1495, 1450,1400,1260, 1150,1105 |
| 2(25) | ![structure: phenyl with COCH3, -NH, 2-CH3] | 2-methyl-4-[N-((o-aminocarbonyl) phenyl)sulfamoyl]phenyl ester of pivalic acid | Rf 0.1 (methylene chloride: ethyl acetate = 30:1 | ν 3450,3200,2970, 1730,1670,1615, 1575,1490,1340, 1280,1220,1150, 1110 |
| 2(26) | ![structure: piperidine with COOH, 2-CH3] | 2-methyl-4-[(2-carboxy) piperidinosulfonyl]phenyl ester of pivalic acid | Rf 0.41 (chloroform: methanol: acetic acid = 100:5:1) | δ 7.7(1H,d),7.75 (1H,s),7.1(1H, d),4.8(1H,b),3.8 (1H,b),3.2(1H, b),2.2(3H,s), 2~1.2(6H,b), 1.35(9H,s) |
| 2(27) | ![structure: phenyl with OH, -NH, 2-CH3] | 2-methyl-4-[N-(o-phenyl)sulfamoyl] phenyl ester of pivalic acid | Rf 0.20 (hexane: ethyl acetate = 5:2) | δ 7.5(2H,b), 7.2~6.5(5H,m), 6.2(2H,b), 2.1(3H,s), 1.3(9H,s) |

TABLE IV-continued

| | | | |
|---|---|---|---|
| 2(28) | ![structure with COOCH2CON(CH3)2, 2-CH3, -NH-phenyl] | 2-methyl-4-[N-(o-(N,N-dimethyl-carbamoylmethoxycarbonyl)phenyl)sulfa moyl]phenyl ester of pivalic acid | Rf 0.51 (chloroform: methanol: acetic acid = 100:5:1) ν 1760,1690,1680, 1490,1590,1410, 1260,1150,1110 |
| 2(29) | —NH—(CH2)2COOH 2-CH3 | 2-methyl-4-[N-(N-carboxyethyl) sulfamoyl]phenyl ester of pivalic acid | Rf 0.33 (chloroform: methanol: acetic acid = 100:5:1) (CDCl3) δ 7.8(1H,s),7.75 (1H,d),7.15(1H, d),5.7(1H,b), 3.25(2H,m),2.6 (2H,t),2.25(3H, s),1.35(9H,s) |
| 2(30) | ![cyclopentyl with COOH and -NH-, 2-CH3] | 2-methyl-4-[N-(o-carboxycyclo-pentyl) sulfamoyl]phenyl ester of pivalic acid | Rf 0.33 (chloroform: methanol = 10:1) (CDCl3) δ 7.8(1H,s),7.75 (1H,d),7.12(1H, d),4.0~3.6(1H, b),2.25(3H,s), 2.1~1.6(6H,b), 1.35(9H,s) |
| 2(31) | ![cyclohexyl with COOH, H (trans), -NH-, 2-CH3] | 2-methyl-4-[N-(o-carboxycyclo-hexyl) sulfamoyl]phenyl ester of pivalic acid | Rf 0.33 (chloroform: methanol = 10:1) (CDCl3) δ 7.65~7.90(2H,m), 7.1(1H,d), 2.25(3H,s), 1.4(9H,s), 1.0~3.0(10H,m) |
| 2(32) | ![phenyl with OCH3, COOH, -NH-, 2-CH3] | 2-methyl-4-[N-(2-methoxy-5-carboxy) sulfamoyl]phenyl ester of pivalic acid | Rf 0.33 (chloroform: methanol: acetic acid = 100:5:1) (CDCl3) δ 8.18(1H,d),7.8 (1H,d,d),7.61(1H, s),7.53(1H,d), 6.95(1H,d),6.75 (1H,d),3.65(3H, s),2.2(3H,s), 1.35(9H,s) |

TABLE IV-continued

| | | | |
|---|---|---|---|
| 2(33) | ![structure: -NH-C6H3(CH3)2 with 2,6-di CH3] | 2,6-dimethyl-4-[N-(p-tolyl)sulfamoyl] phenyl ester of pivalic acid | Rf 0.44 (methylene chloride: ethyl acetate = 30:1) | ν 1750,1470,1390, 1330,1280,1140, 1100 |
| 2(34) | ![structure: -NH-C6H4-CH2OH] | 4-[N-(o-hydroxymethylphenyl) sulfamoyl]phenyl ester of pivalic acid | Rf 0.76 (ethyl acetate: hexane = 2:1) | ν 3470,3050,2950, 2850,1750,1590, 1470,1320,1210 |
| 2(35) | ![structure: cyclopentyl with COOH, -NH-, -H, 2-CH3] | 2-methyl-4-[N-(trans-o-carboxy-cyclopentyl)sulfamoyl]phenyl ester of pivalic acid | Rf 0.33 (chloroform: methanol = 10:1) | (CDCl3) δ 7.75(1H,s),7.7 (1H,d),7.1(1H, d),3.75(1H,m), 2.5(1H,m),2.25 (3H,s),2.4~1.4 (6H,m),1.4(9H,s) |
| 2(36) | ![structure: cyclopentyl with COOH, -NH-, 2-CH3] | 2-methyl-4-[N-(cis-o-carboxyl-cyclopentyl)sulfamoyl]phenyl ester of pivalic acid | Rf 0.33 (chloroform: methanol = 10:1) | (CDCl3 + CD3OD) δ 7.75(1H,s),7.7 (1H,d),7.1(1H, d),3.75(1H,m), 2.8(1H,m),2.25 (3H,s),2.0~1.4 (6H,m),1.4(9H,s) |
| 2(37) | ![structure: cyclohexyl with COOH, H, -NH-, 2-CH3] | 2-methyl-4-[N-cis-o-carboxy-cyclohexyl)sulfamoyl]phenyl ester of pivalic acid | Rf 0.18 (chloroform: methanol = 10:1) | ν 3260,2400~2700, 1740,1700,1470, 1420,1330 |
| 2(38) | ![structure: -NH-C6H4-COOCH2CON(C2H5)2, 2-CH3] | 2-methyl-4-[N-(o-(N,N-diethyl-carbamoylmethoxycarbonyl)phenyl) sulfamoyl]phenyl ester of pivalic acid | Rf 0.55 (methylene chloride: ethyl acetate = 30:1) | ν 3160,3000,1755, 1670,1590,1490, 1270,1100,940 |

TABLE IV-continued

| | Structure (R) | Compound name | Rf / IR | NMR |
|---|---|---|---|---|
| 2(39) | phenyl with SO$_2$NH$_2$, -NH-, 2-CH$_3$ | 2-methyl-4-[N-(o-sulfamoylphenyl)sulfamoyl]phenyl ester of pivalic acid | ν 1750, 1720, 1590, 1570, 1460 | |
| 2(40) | phenyl with COOH, -NH-, 2-CH$_3$ | 2-methyl-4-[N-(m-carboxyphenyl)sulfamoyl]phenyl ester of pivalic acid | Rf 0.20 (chloroform: methanol: acetic acid = 100:5:1) | (CDCl$_3$ + CD$_3$OD) δ 7.75~7.4(3H,m), 7.4~7.1(3H,m), 6.97(1H,d), 2.15(3H,s), 1.35(9H,s) |
| 2(41) | phenyl with CH$_2$COOH, -NH-, -H | 4-[N-(m-carboxymethylphenyl)sulfamoyl]phenyl ester of pivalic acid | Rf 0.33 (chloroform: methanol: acetic acid = 100:5:1) | (CDCl$_3$ + CD$_3$OD) δ 7.7(2H,d), 7.2~6.8(6H,m),3.45(2H,s), 1.30(9H,s) |
| 2(42) | phenyl with CH$_2$COOH, -NH-, 2-CH$_3$ | 2-methyl-4-[N-(m-carboxymethylphenyl)sulfamoyl]phenyl ester of pivalic acid | Rf 0.33 (chloroform: methanol: acetic acid = 100:5:1) | (CDCl$_3$ + CD$_3$OD) δ 7.55(1H,s), 7.5(1H,d), 7.2~6.8(5H,m), 3.45(2H,s), 2.15(3H,s), 1.35(9H,s) |
| 2(43) | phenyl with (CH$_2$)$_2$COOH, -NH-, 2-CH$_3$ | 2-methyl-4-[N-(m-carboxyethylphenyl)sulfamoyl]phenyl ester of pivalic acid | Rf 0.31 (chloroform: methanol: acetic acid = 100:5:1) | (CDCl$_3$) δ 7.62(1H,s),7.5 (1H,d),7.25~6.9 (4H,m),6.75(1H, b),6.6(1H,b), 2.8(2H,t),2.6 (2H,t),2.2(3H,s), 1.35(9H,s) |

TABLE IV-continued

| | | | | |
|---|---|---|---|---|
| 2(44) | [structure: 4-Cl, 3-NH-, 5-COOH phenyl with 2-CH₃] | 2-methyl-4-[N-(2-chloro-5-carboxyphenyl)sulfamoyl]phenyl ester of pivalic acid | Rf 0.34 (chloroform: methanol: acetic acid = 100:5:1) | (CDCl₃ + CD₃OD) δ 8.2(1H,b), 7.8~7.45(3H,b), 7.3(1H,d), 7.0(1H,d), 2.2(3H,s), 1.35(9H,s) |
| 2(45) | [structure: 3-(CH₂)₂COOH, NH-, H phenyl] | 4-[N-(m-carboxyethylphenyl)sulfamoyl]phenyl ester of pivalic acid | Rf 0.27 (chloroform: methanol: acetic acid = 100:5:1) | (CDCl₃) δ 7.65(2H,d), 7.1(2H,d), 7.35~6.8(2H,m), 6.8~6.6(2H,d), 2.85(2H,t),2.55 (2H,t),1.35(9H,s) |
| 2(46) | [structure: 3-SO₃H, NH- phenyl] | 2-methyl-4-[N-(m-sulfonyl)sulfamoyl] phenyl ester of pivalic acid | Rf 0.35 (chloroform: methanol: acetic acid = 10:3:1) | (CD₃SOCD₃) δ 7.7~7.6(2H,m), 7.4~6.9(5H,m), 2.15(3H,s), 1.30(9H,s) |
| 2(47) | [structure: 2-SO₃H, 4-CH, NH- phenyl with 2-CH₃] | 2-methyl-4-[N-(2-sulfo-4-methylphenyl)sulfamoyl]phenyl ester of pivalic acid | Rf 0.44 (chloroform: methanol: acetic acid = 100:3:1) | (CDCl₃ + CD₃OD) δ 7.9~7.5(3H,m), 7.5~6.9(3H,m), 2.3(3H,s), 2.2(3H,s), 1.35(9H,s) |
| 2(48) | [structure: 3-OCH₂COOH, NH- phenyl with 2-CH₃] | 2-methyl-4-[N-(m-carboxymethoxyphenyl)sulfamoyl] phenyl ester of pivalic acid | Rf 0.39 (chloroform: methanol: acetic acid = 30:3:1) | (CDCl₃) δ 7.55(1H,s), 7.5(1H,d), 7.32~6.5(5H,m), 6.2(1H,bs), 4.45(2H,s),2.2 (3H,s),1.37(9H,s) |

TABLE IV-continued

| | | | |
|---|---|---|---|
| 2(49) | 2-0methyl-4-[N-(1,4-dioxa-2-carboxy-8-yl-naphthalene)sulfamoyl]phenyl ester of pivalic acid | Rf 0.27 (chloroform: methanol: acetic acid = 30:3:1) | (CDCl$_3$) δ 7.6(1H,s),7.5 (1H,d),7.35(1H, d),7.2(1H,d,d), 6.9(1H,d),6.85 (1H,d),4.7(1H,s), 4.5(1H,d),4.1(1H, d,d),2.1(1H,s) 1.38(1H,s) |
| 2(50) | N-[m-(3-methyl-4-pivaloyloxy-benzene)sulfonylaminobenzoyl] glycine | Rf 0.26 (chloroform: methanol: acetic acid = 30:3:1) | (CDCl$_3$ + CD$_3$OD) δ 7.6~6.9(7H,m), 4.1(2H,s), 2.15(3H,s), 1.35(9H,s) |
| 2(51) | 2-methyl-4-[N-(o-carboxypropoxy-phenyl)sulfamoyl]phenyl ester of pivalic acid | Rf 0.45 (chloroform: methanol: acetic acid = 100:5:1) | (CDCl$_3$ + CD$_3$OD) δ 7.6~7.3(3H,m), 7.1~6.5(4H,m), 3.8(2H,t),2.4 (2H,t),2.15(3H, s),2.02(2H,q), 1.35(9H,s) |

TABLE IV

| | | | |
|---|---|---|---|
| 2(53) | ![structure: phenyl ring with CONHCH₂COOH and -NH-, 2-CH₃] | N-[o-(3-methyl-4-pivaloyloxy-benzene) sulfonylaminobenzoyl]glycine | Rf 0.41 (chloroform: methanol: acetic acid = 30:3:1) <br> ν 2970,1740,1630, 1600,1520,1480, 1390,1330,1260, 1230,1150,1090, 930,760,590 |
| 2(54) | ![structure: 1,4-benzodioxane connected to tetrazole with sulfamoyl, 2-CH₃] | 2-methyl-4-[N-(1,4-dioxa-2-tetrazolyl-8-yl-naphthalene) sulfamoyl]phenyl ester of pivalic acid | Rf 0.46 (chloroform: methanol: acetic acid = 30:3:1) <br> (CDCl₃) δ 7.6(1H,s), 7.5(1H,d), 7.3~6.7(4H,m), 5.2(1H,fou), 4.5(2H,cig), 2.1(3H,s), 1.4( 9H,s) |
| 2(55) | ![structure: phenyl with CONH-CH(COOH)-CH(CH₃)₂ valine, -NH-, 2-CH₃] | N-[o-(3-methyl-4-pivaloyloxy-benzene)sulfonylaminobenzoyl]-L-valine | Rf 0.44 (chloroform: methanol: acetic acid = 100:5:1) <br> (CDCl₃) δ 7.80(1H,d), 7.32~7.24(4H,m), 7.15(1H,t),7.0 (1H,d),6.4(1H, d),4.5(1H,q),2.3 (1H,m),2.1(3H,s), 1.35(9H,s) |
| 2(56) | ![structure: 5-chloro phenyl with CONHCH₂COOH, -NH-, 2-CH₃, Cl] | N-[5-chloro-2-(3-methyl-4-pivaloyloxybenzene)sulfonylamino-benzoyl]glycine | Rf 0.29 (chloroform: methanol: acetic acid = 100:5:1) <br> (CDCl₃ + CD₃OD) δ 7.8~6.9(7H,m), 3.95(2H,s), 2.15(3H,s), 1.35(9H,s) |

TABLE IV-continued

| | Structure | Name | Rf | NMR |
|---|---|---|---|---|
| 2(57) | [structure: phenyl with -NH-, CH₃/COOH branch, CONH-, 2-CH₃] | N-[o-(3-methyl-4-pivaloyloxy-benzene)sulfonylaminobenzoyl]-dl-alanine | Rf 0.24 (chloroform: methanol: acetic acid = 100:5:1) | (CDCl₃) δ 7.75(1H,d),7.6 (1H,s),7.65~7.4 (2H,m),7.3~7.05 (2H,m),7.0(1H,d),6.55(1H,d), 4.6(1H,q),2.1 (3H,s),2.5(3H,d), 1.35(9H,s) |
| 2(58) | [structure: phenyl with -NH-, CONH-(CH₂)₂COOH, 2-CH₃] | N-[o-(3-methyl-4-pivaloyloxy-benzene)sulfonylaminobenzoyl]-β-alanine | Rf 0.36 (chloroform: methanol: acetic acid = 100:5:1) | (CDCl₃) δ 7.75(1H,d),7.6 (1H,s),7.55~7.2 (3H,m),7.1(1H,t),6.95(1H,d),6.6 (1H,b),3.5(2H,q), 2.6(2H,q),2.1(3H,s),1.35(9H,s) |
| 2(59) | [structure: phenyl with -NH-, COOCH₂-phenyl, NO₂, 2-CH₃] | 2-methyl-4-[N-(2-benzyloxycarbonyl-5-nitrophenyl)sulfamoyl]phenyl ester of pivalic acid | Rf 0.27 (ethyl acetate: hexane = 1:5) | (CDCl₃) δ 8.5(1H,d), 8.1(1H,d), 7.75(3H,m), 7.4(5H,s), 7.1(1H,d), 5.4(2H,s) |
| 2(60) | [structure: phenyl with -NH-, CONHCH₂COOH, OC₅H₁₁, 2-CH₃] | N-[2-((3-methyl-4-pivaloyloxybenzene)sulfonylamino)-5-penthyloxybenzoyl]glycine | Rf 0.22 (ethyl acetate: hexane: acetic acid = 10:10:0.5) | (CD₃OD) δ 7.3~7.6(3H,m), 6.9~7.2(3H,m), 3.95(2H,t), 3.9(2H,s), 2.15(3H,s) |
| 2(61) | [structure: phenyl with -NH-, CONHCH₂COOH, OC₁₀H₂₁, 2-CH₃] | N-[5-decyloxy-2-(3-methyl-4-pivaloyloxybenzene)sulfonylamino-benzoyl]glycine | Rf 0.25 (ethyl acetate: hexane: acetic acid = 100:10:0.5) | (CDCl₃) δ (9H,s) |

TABLE IV-continued

| # | Structure | Name | Rf | NMR |
|---|---|---|---|---|
| 2(62) | [cyclic structure with CON-phenyl-NH, 2-CH₃, COOH] | 2-methyl-4-[N-(2-prolylcarbonylphenyl)sulfamoyl] phenyl ester of pivalic acid | Rf 0.18 (chloroform: methanol: acetic acid = 100:5:1) | (CDCl₃) δ 8.65(1H,s),7.8~7.63(3H,m),7.4~7.0(5H,m),4.6(1H,m),3.25(2H,t), 2.3~2.1(2H,m), 2.15(3H,s),2.0~1.7(2H,m),1.35 (9H,s) |
| 2(63) | [phenyl-CONHCH₂—COOH, —NH—, —H] | N-[o-(p-pivaloyloxybenzene) sulfonylaminobenzoyl]glycine | Rf 0.14 (chloroform: methanol: acetic acid = 100:5:1) | (CDCl₃ + CD₃OD), δ 7.8~7.0(8H,m), 3.95(2H,s), 1.30(9H,s) |
| 2(64) | [phenyl-CONHCH₂COOH, CH₃, —NH—, 2-CH₃] | N-[2-(3-methyl-4-pivaloyloxybenzene) sulfonylamino-5-methylbenzoyl]glycine | Rf 0.20 (chloroform: methanol: acetic acid = 100:5:1) | (CDCl₃) δ 7.7~6.8(6H,m), 6.3(1H,b), 4.0(2H,d), 2.3(3H,s), 2.1(3H,s), 1.3(9H,s) |
| 2(65) | [phenyl-CONHCHCOOH with CH₃, —NH—, 2-CH₃] | N-[o-(3-methyl-4-pivaloyloxybenzene) sulfonylaminobenzoyl]-l-alanine | Rf 0.24 (chloroform: methanol: acetic acid = 100:5:1) | (CDCl₃) δ 7.8~6.9(7H,m), 6.5(1H,b), 4.6(1H,m), 2.1(3H,s), 1.45(3H,d), 1.35(9H,s) |
| 2(66) | [Cl-phenyl-CONHCCHCOOH with CH₃, —NH—, 2-CH₃] | N-[5-chloro-2-(3-methyl-4-pivaloyloxybenzene)sulfonylamino benzoyl]-l-alanine | Rf 0.3 (chloroform: methanol: acetic acid = 100:5:1) | (CDCl₃) δ 7.75(1H,d),7.55 (1H,s),7.5~7.3 (3H,m),6.95(1H,d),6.44(1H,b), 4.55(1H,m),2.15 (3H,s),1.45(3H, d),1.35(9H,s) |

TABLE IV-continued

| | | | |
|---|---|---|---|
| 2(67) | 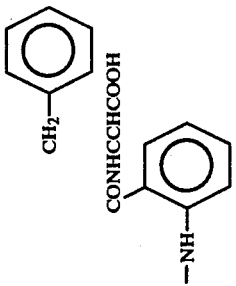 | N-[o-(3-methyl-4-pivaloyloxybenzene)sulfonylaminobenzoyl]-L-phenylalanine | Rf 0.30 (ethyl acetate: hexane: acetic acid = 10:10:0.5) | (CD$_3$OD) δ 6.95~7.7(12H,m), 4.6~4.8(1H,m), 3.0~3.4(2H,m), 2.1(3H,s), 1.35(9H,s) |
| 2(68) | 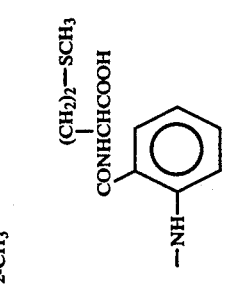 | N-[o-(3-methyl-4-pivaloyloxybenzene)sulfonylaminobenzoyl]-dl-methionine | Rf 0.29 (ethyl acetate: hexane: acetic acid = 10:10:0.5) | (CD$_3$OD) δ 7.55~7.8(4H,m), 7.45(1H,t),7.0~7.2 (2H,m),4.6~4.7(1H, m),2.4~2.6(2H,m), 2.13(3H,s),2.10(3H, s),2.0~2.3(2H,m), 1.35(9H,s) |
| 2(69) | 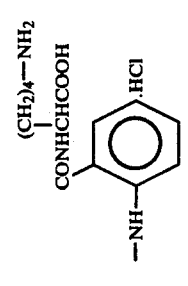 | N-[o-(3-methyl-4-pivaloyloxybenzene)sulfonylaminobenzoyl]-L-lysin. hydrochloride | Rf 0.73 (ethyl acetate: acetic acid: water = 3:1:0.5) | (CD$_3$OD) δ 7.57~7.80(3H,m), 7.35~7.55(2H,m), 7.0~7.22(2H,m), 4.45~4.65(1H,m), 2.95(2H,t),2.15(3H, s),1.4~2.1(6H,m), 1.35(9H,s) |
| 2(70) | 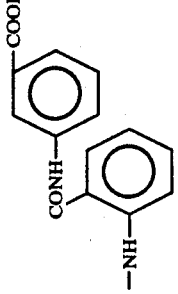 | 2-methyl-4-[N-(2-(N-carboxyphenyl-3-yl)carbamoylphenyl)sulfamoyl] phenyl ester of pivalic acid | Rf 0.52 (ethyl acetate: hexane: acetic acid = 10:10:0.5) | ν 1750,1690,1540, 1480,1330,1300, 1230,1150,1110 |

TABLE IV-continued

| | Structure | Name | Rf | NMR/IR |
|---|---|---|---|---|
| 2(71) | OCH₂COOH on phenyl with –NH–, 2-CH₃ | 2-methyl-4-[N-(2-carboxymethoxyphenyl)sulfamoyl]phenyl ester of pivalic acid | Rf 0.21 (chloroform:methanol:acetic acid = 30:3:1) | (CDCl₃) δ 7.7~6.6(8H,m), 4.5(2H,s), 2.15(3H,s), 1.3(9H,s) |
| 2(72) | CONH(CH₂)₂COOH, Cl, –NH–, 2-CH₃ | N-[5-chloro-2-(3-methyl-4-pivaloyloxybenzene)sulfonylaminobenzoyl]-β-alanine | Rf 0.28 (chloroform:methanol:acetic acid = 100:5:1) | (CDCl₃) δ 7.8~7.2(5H,m), 7.0(1H,d), 7.6(1H,d), 3.6(2H,q), 2.64(2H,t), 2.2(3H,s), 1.35(9H,s) |
| 2(73) | CONH(CH₂)₃COOH, Cl, –NH–, 2-CH₃ | 2-methyl-4-[N-((2-carboxypropylcarbamoyl-4-chloro)phenyl)sulfamoyl]phenyl ester of pivalic acid | Rf 0.28 (chloroform:methanol:acetic acid = 100:5:1) | (CDCl₃) δ 7.8~7.2(5H,m), 7.0(1H,d),6.4(1H,b),3.3(2H,q),2.5(2H,t), 2.15(3H,s), 1.9(2H,m), 1.35(9H,s) |
| 2(74) | phenyl–COOH, CONH, phenyl–NH–, 2-CH₃ | 2-methyl-4-[N-(2-(N-carboxyphenyl)carbamoyl)phenyl)sulfamoyl] phenyl ester of pivalic acid | Rf 0.54 (ethyl acetate:hexane:acetic acid = 10:10:0.5) | ν 1750,1680,1650, 1590,1520,1480, 1400,1320,1280, 1250,1220 |
| 2(75) | CONHCH₂COOH, Cl, –NH–, H | N-[2-(p-pivaloyloxybenezene)sulfonylamino-5-chlorobenzoyl]glycine | Rf 0.23 (chloroform:methanol:acetic acid = 100:5:1) | (CDCl₃) δ 7.7(2H,d), 7.8~7.6(1H,m), 7.5~7.4(2H,m), 7.08(2H,b), 6.3(0H,b), 4.08(2H,d), 1.35(9H,s) |

TABLE IV-continued

| | | | |
|---|---|---|---|
| 2(76) | N-[O-(3-methyl-4-pivaloyloxybenezene)sulfonylaminobenzoyl]tyrosine | Structure: phenol with CH₂ group; CONHCHCOOH; —NH attached to benzene with 2-CH₃ | Rf 0.27 (ethyl acetate: hexane: acetic acid = 10:10:0.5) (CD3OD) δ 7.32~7.7(5H,m), 7.0~7.2(2H,m),7.05 (2H,d),6.7(2H,d), 2.6~2.75(1H,m), 2.87~4.25(2H,m), 2.12(3H,s), 1.35(9H,s) |
| 2(77) | N-[-(3-methyl-4-pivaloyloxybenezene)sulfonylaminophenylacethyl]glycine | CH₂CONHCH₂COOH; —NH; 2-CH₃ | Rf 0.44 (ethyl acetate: acetic acid = 25:1) (CD3OD) δ 7.5~7.7(2H,m), 7.0~7.35(5H,m), 3.9(2H,2), 3.37(2H,s), 2.2(3H,s), 1.41(9H,s) |
| 2(78) | N-[O-(4-pivaloyloxybenezene)sulfonylaminophenylacetyl]glycine | CH₂CONHCH₂COOH; —NH; —H | Rf 0.37 (ethyl acetate: acetic acid = 25:1) ν 1750,1610,1530, 14,80,1400 |
| 2(79) | 4-[N-((2-carboxypropylcarbamoyl-4-chloro)phenyl)sulfamoyl]phenyl ester of pivalic acid | CONH(CH₂)₃COOH; Cl; —NH; —H | Rf 0.47 (chloroform: methanol: acetic acid = 100:5:1) (CDCl₃ + CD3OD) δ 7.7(2H,d),7.5 (1H,s),7.4~7.2 (2H,m),7.1(2H,d), 3.2(2H,t), 2.3(2H,t), 1.8(2H,m), 1.3(9H,s) |
| 2(80) | N-[5-methylthio-2-(p-pivaloyloxy-benezene)sulfonylaminobenzoyl]glycine | CONHCH₂COOH; SCH₃; —NH; —H | Rf 0.34 (chloroform: methano;: acetic acid = 30:3:1) (CDCl3 + CD3OD) δ 7.7(2H,d), 7.6(1H,d), 7.4~7.2(2H,m), 7.1(2H,d), 3.98(2H,s), 2.53(3H,s), 1.4(9H,s) |

TABLE IV-continued

| | | | | |
|---|---|---|---|---|
| 2(81) | CONHCH₂COOH / -NH- / CF₃ / 2-CH₃ | N-[2-(3-methyl-4-pivaloyloxybenzene) sulfonylamino-4-trifluoromethylbenzoyl]glycine | Rf 0.12 (ethyl acetate: hexane: acetic acid = 10:10:0.5) | (CD3OD) δ 7.92(1H,s),7.80 (1H,d),7.55~7.7 (2H,m),7.45 (1H,d),7.11(1H,d), 4.0(2H,s), 2.16(3H,s), 1.36(9H,s) |
| 2(82) | CONHCH₂COOH / -NH- / CF₃ | N-[2-(p-pivaloyloxybenzene) sulfonylamino-4-trifluoromethylbenzoyl]glycine | Rf 0.12 (ethyl acetate: hexane acetic acid = 10:10:0.5) | (CD3OD) δ 7.95(1H,s), 7.77(2H,d), 7.80(1H,d), 7.45(1H,d), 7.20(2H,d), 4.0(2H,s), 1.33(9H,s) |
| 2(83) | CH₂—SCH₃ / CONHCHCOOH / -NH- / -H | N-[O-(p-pivaloyloxybenzene) sulfonylaminobenzoyl]-S-methyl-L-cysteine | Rf 0.27 (chloroform: methanol: acetic acid = 100:5:1) | (CDCl3 + CD3OD) δ 7.8(2H,d), 7.7~7.2(3H,m), 7.1(2H,d), 7.11(1H,d), 4.8(1H,m), 3.05(2H,m),2.15 (3H,s),1.3(9H,s) |
| 2(84) | (CH₂)₂—SCH₃ / CONHCHCOOH / -NH- / -H | N-[2-(4-pivaloyloxybenzene) sulfonylaminobenzoyl]-L-methionine | Rf 0.34 (chloroform: methanol: acetic acid = 100:5:1) | (CDCl3 + CD3OD) δ 7.8(2H,d), 7.7~7.2(3H,m), 7.1(2H,d), 7.11(1H,d), 4.7(1H,m),2.8~2.0 (4H,m),2.14(3H,s), 1.3(9H,s) |
| 2(85) | CONHCH₂COOH / -NH- / -OC₁₀H₂₁ / -H | N-[5-decyloxy-2-(p-pivaloyloxybenzene) sulfonylaminobenzoyl]glycine | Rf 0.49 (ethyl acetate: hexane: acetic acid = 10:10:0.5) | ν 3449,2926,1762, 1728,1645,1607, 1530,1501,1252 |

TABLE IV-continued

| # | Structure | Name | Rf | NMR |
|---|---|---|---|---|
| 2(86) | CONHCH₂COOH / phenyl ring with 2-CH₃, —NH, S—CH₃ | N-[2-(3-methyl-4-pivaloyloxybenzene)sulfonylamino-5-methylthiobenzoyl]glycine | Rf 0.25 (chloroform:methanol:acetic acid = 100:5:1) | (CDCl₃+CD₃OD) δ 7.7~7.2(5H,m), 6.95(1H,d), 2.95(2H,s), 2.5(3H,s), 2.2(3H,s), 1.35(9H,s) |
| 2(87) | CONHCH₂COOH / phenyl ring with —H, —NH, S—(CH₂)₂CH₃ | N-[2-(p-pivaloyloxybenzene)sulfonylamino-5-propylthiobenzoyl]glycine | Rf 0.29 (chloroform:methanol:acetic acid = 100:5:1) | (CDCl₃+CD₃OD) δ 7.75(2H,d), 7.6~7.1(3H,m), 7.1(2H,d), 4.0(2H,s), 2.9(2H,t), 1.8~1.5(2H,m),1.35(9H,s),1.0(3H, t) |
| 2(88) | CONH—CHCOOH—phenyl / phenyl ring with —H, —NH | N-[O-(p-pivaloyloxybenzoyl)]-2R-phenylglycine | Rf 0.19 (ethyl acetate:hexane:acetic acid = 10:10:0.5) | (CD₃OD) δ 7.55~7.7(4H,m), 7.2~7.7(6H,m), 7.15(1H,t), 6.97(2H,d), 5.57(1H,s), 1.3(9H,s) |
| 2(89) | CONH—CHCOOH—phenyl / phenyl ring with —H, —NH | N-[O-(3-methyl-4-pivaloyloxybenzoyl]-2R-sulfonylaminobenzoyl]-2R-phenylglycine | Rf 0.2 (ethyl acetate:hexane:acetic acid = 10:10:0.5) | (CD₃OD) δ 7.2~7.8(10H,m), 7.12(1H,t), 6.90(1H,d), 5.57(1H,s), 2.06(3H,s), 1.35(9H,s) |
| 2(90) | CONHCH₂COOH / phenyl ring with 2-CH₃, —NH, CH₃ | N-[5-methyl-2-(p-pivaloyloxybenzene)sulfonylamino-benzoyl]glycine | Rf 0.27 (chloroform:methanol:acetic acid = 100:5:1) | (CDCl₃+CD₃OD) δ 7.7(2H,d), 7.5(1H,s), 7.3~7.1(2H,b), 7.02(2H,d), 3.95(2H,s), 2.3(3H,s), 1.3(9H,s) |

TABLE IV-continued

| | Structure | Substituent | Name | Rf | Spectrum |
|---|---|---|---|---|---|
| 2(91) | [structure: phenyl-CONH-phenyl with COOH] | —H | 4-[N-(O-(N-carboxyphenyl-3-yl)carbamoylphenyl)sulfamoyl]phenyl ester of pivalic acid | Rf 0.32 (chloroform: methanol: acetic acid = 100:5:1) | ν 1752,1692,1646, 1595,1554,1491, 1409,1338,1304, 1259,1209 |
| 2(92) | [structure: phenyl-CONHCH₂COOCH₃ with —NH] | —H | N-[2-(p-pivaloyloxybenzene)sulfonylaminobenzoyl]glycine methyl ester | Rf 0.77 (chloroform: methanol: = 10:1) | (CDCl₃) δ 7.7(2H,d), 7.65(1H,b), 7.55~7.3(2H,m), 7.2~7.0(1H,m), 7.0(2H,d), 4.0(2H,d),3.8 (3H,s),1.35(9H,s) |
| 2(93) | [structure: phenyl-CONHCH₂COOCH₂-CON(CH₃)₂ with —NH] | —H | 2-[N-(2-(4-pivaloyloxybenzene)sulfonylaminobenzoyl)glycyclocyl-N,N-dimethylacetamide | Rf 0.53 (chloroform: methanol: = 10:1) | (CDCl₃) δ 7.7(2H,d), 7.8~7.6(1H,b), 7.55~7.2(2H,m), 7.2~7.0(1H,m), 7.05(2H,d),4.8 (2H,s),4.2(2H,d), 3.0(6H,s),1.35(9H,s) |
| 2(94) | [structure: phenyl-CONHCH₂COOH with OC₅H₁₁ and —NH] | —H | N-[5-pentyloxy-2-(p-pivaloyloxybenzene)sulfonylaminobenzoyl]glycine | Rf 0.26 (ethyl acetate: hexane: acetic acid = 10:10:0.5) | (CDCl₃) δ 7.65(2H,d),7.50 (1H,d),7.18(2H,d), 7.11(1H,s),7.02(1H,dd),3.95(2H,t),3.88 (2H,s),1.65~1.85(2H,m),1.25~1.55(4H,m), 1.33(9H,s),1.92(3H,t) |
| 2(95) | [structure: phenyl-COOCH₂-phenyl with Cl and —NH] | 2-CH₃ | 2-methyl-4-[N-((2-benzyloxy-carbonyl-4-chloro)phenyl)sulfamoyl]phenyl ester of pivalic acid | Rf 0.30 (ethyl acetate: hexane: = 1:10) | |

TABLE IV-continued
| | | | |
|---|---|---|---|
| 2(96) | 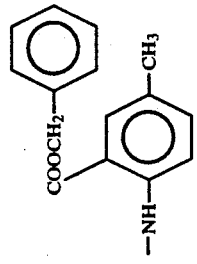<br>2-CH₃ | 2-methyl-4-[N-((2-benzyloxy-carbonyl-4-methyl)phenyl)sulfamoyl]phenyl ester of pivalic acid | Rf 0.28 (ethyl acetate: hexane: = 1:10) |
| 2(97) | 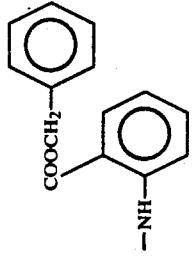<br>2-CH(CH₃)₂ | 2-isopropyl-4-[N-(o-benzyloxycarbonyl)phenyl]sulfamoyl]phenyl ester of pivalic acid | Rf 0.32 (ethyl acetate: hexane: = 1:10) |

TABLE IV

| | Structure | Name | Rf |
|---|---|---|---|
| 2(98) | (structure: COOCH₂-phenyl; phenyl-NH with Cl at 4-position; 2-CH(CH₃)₂) | 2-isopropyl-4-[N-((2-benzyloxycarbonyl-4-chloro)phenyl)sulfamoyl]phenyl ester of pivalic acid | Rf 0.35 (ethyl acetate: hexane: = 1:10) |
| 2(99) | (structure: naphthalene with COOCH₂-phenyl and NH; 2-CH₃) | 2-methyl-4-[N-(2-benzyloxycarbonylphenyl)sulfamoyl]phenyl ester of pivalic acid | Rf 0.58 (ethyl acetate: hexane: = 1:10) |
| 2(100) | (structure: phenyl with two COOCH₂-phenyl groups and NH; 2-CH₃) | 2-methyl-4-[N-(2,5-dibenzyloxycarbonylphenyl)sulfamoyl]phenyl ester of pivalic acid | Rf 0.12 (ethyl acetate: hexane: = 1:10) |
| 2(101) | (structure: pyridine with COOCH₂-phenyl and NH; 2-CH₃) | 2-methyl-4-[N-(3-benzyloxycarbonylphenyl)sulfamoyl]phenyl ester of pivalic acid | Rf 0.37 (ethyl acetate: hexane: = 2:5) |

TABLE IV-continued

| | | | |
|---|---|---|---|
| 2(102) | [structure: phenyl-COOCH2-phenyl with -NH and -OH, OH at 4-position] 2-CH3 | 2-methyl-4-[N-(2-benzyloxycarbonyl-4-hydroxy)phenyl)sulfamoyl] phenyl ester of pivalic acid | Rf 0.18 (methylene chloride: methanol = 10:1) |
| 2(103) | [structure: phenyl-COOCH2-phenyl with -NH] 2,6-diCH3 | 2,6-dimethyl-4-[N-(o-benzyloxycarbonylphenyl)sulfamoyl] phenyl ester of pivalic acid | |
| 2(104) | [structure: phenyl-COOCH2-phenyl with -NH and -OCOCH3] 2-CH3 | 2-methyl-4-[N-((4-acetyloxy-2-benzyloxycarbonyl)phenyl)sulfamoyl] phenyl ester of pivalic acid | Rf 0.39 (chloroform: methanol = 10:1) |
| 2(105) | [structure: phenyl-COOCH2-phenyl with -NH and -OCO(CH2)4CH3] 2-CH3 | 2-methyl-4-[N-((2-benzyloxycarbonyl)-4-hexanoyloxy)phenyl)sulfamoyl] phenyl ester of pivalic acid | Rf 0.44 (mchloroform: methanol = 10:1) |

TABLE IV-continued

| | | | |
|---|---|---|---|
| 2(106) | ![structure: phenyl ring with -NH-, two COOCH2-phenyl groups at 2,6 positions] | 2-methyl-4-[N-(2,6-dibenzyloxy-carbonyl)phenyl)sulfamoyl]phenyl ester of pivalic acid | Rf 0.12 (hexane: ethyl acetate = 10:1) |
| | 2-CH₃ | | |
| 2(107) | ![structure: phenyl-NH with COOCH2-COOCH2-phenyl] | o-(3-methyl-4-pivaloyloxybenzene)sulfonylaminobenzoyloxy acetic acid benzylester | Rf 0.41 (hexane: ethyl acetate = 5:2) |
| | 2-CH₃ | | |
| 2(114) | ![structure: phenyl-CH(COOH)-CONH-phenyl-NH-] | N-[o-(p-pivaloyloxybenzene)sulfonylaminobenzoyl]-2S-phenyl glycine | Rf 0.31 (ethyl acetate: hexane: acetic acid = 10:10:0.5) ν 1751,1641,1594, 1520,1493,1456, 1398,1340,1275, 1207,1164,1104 |
| | —H | | |

TABLE IV-continued

| | | | | |
|---|---|---|---|---|
| 2(115) | N-[o-(p-pivaloyloxybenzene) sulfonylaminobenzoyl]-L-leucine | CONHCHCOOH — CH₂CH(CH₃)₂ / —NH— / —H | Rf 0.45 (Chloroform: methanol: acetic acid = 100:5:1) | (CDCl₃) δ 7.75(2H,d), 7.85~7.60(1H,m), 7.6~7.15(3H,m), 7.05(2H,d),6.40 (1H,b),5.4(1H,b), 4.6(1H,m),2.0~1.4 (3H,b),1.35(9H,s), 1.0(6H,d) |
| 2(116) | N-[o-(p-pivaloyloxybenzene) sulfonylaminobenzoyl]glycinamide | CONHCH₂CONH₂ / —NH— / —H | Rf 0.28 (chloroform: methanol acetic acid = 100:5:1) | (CDCl₃ + CD₃OD + CD₃SOCD₃) δ 7.75(2H,d), 7.65~7.35(3H,m), 7.1(2H,d), 7.2~7.0(1H,b), 3.95(2H,s), 1.35(9H,s) |
| 2(117) | N-[o-(p-pivaloyloxybenzene) sulfonylaminobenzoyl]-L-alanine | CONHCHCOOH — CH₃ / —NH— / —H | Rf 0.28 (chloroform: methanol acetic acid = 100:5:1) | (CDCl₃) δ 7.75(2H,d), 7.8~7.7(1H,b), 7.5~7.4(2H,m), 7.05(2H,d),7.2~ 7.1(1H,m),6.5(1H,d),4.6(1H,q),1.5 (3H,d),1.35(9H,s) |
| 2(118) | N-[o-(p-pivaloyloxybenzene) sulfonylaminobenzoyl]-β-alanine | CONH(CH₂)₂COOH / —NH— / —H | Rf 0.48 (Chloroform: methanol: acetic acid = 100:5:1) | (CDCl₃) δ 7.7(2H,d), 7.8~7.7(1H,b), 7.45(1H,t),7.3 (1H,d),7.2(1H,t), 7.1(1H,d),7.05 (2H,d),6.6(1H,b), 3.5(2H,q),2.6 (2H,t),1.35(9H,s) |
| 2(119) | p-[N-(o-carboxyethoxyphenyl) sulfamoyl]phenyl ester of pivalic acid | O(CH₂)₂COOH / —NH— / —H | Rf 0.36 (chloroform: methanol: acetic acid = 100:5:1) | (CDCl₃) δ 7.7(2H,d), 7.75~7.65(1H,b), 7.2~7.0(5H,m), 6.8(1H,d), 4.0(2H,t), 2.6(2H,t), 1.35(9H,s) |

TABLE IV-continued

| | Structure | Name | Rf | NMR/IR |
|---|---|---|---|---|
| 2(120) | CH(CH₃)₂<br>CONH—COOH<br>[phenyl ring]<br>—NH<br>—H | N-[o-(p-pivaloyloxybenzene)sulfonylaminobenzoyl]-S-valine | Rf 0.34<br>(acetic acid:<br>chloroform =<br>1:19) | ν 2972,1752,1640,<br>1595,1527,1492,<br>1398 |
| 2(121) | O(CH₂)₃COOH<br>[phenyl ring]<br>—NH<br>—H | p-[N-(o-carboxypropoxyphenyl)sulfamoyl]phenyl ester of pivalic acid | Rf 0.48<br>(Chloroform:<br>methanol:<br>acetic acid =<br>100:5:1) | (CDCl₃)<br>δ 7.7(2H,d),<br>7.45(1H,d,d),<br>7.0(2H,d),<br>7.1~6.5(5H,m),<br>3.8(2H,t),<br>2.4(2H,t),<br>2.0(2H,b),<br>1.35(9H,s) |
| 2(122) | CH₃<br>N—CH₂COOH<br>CO<br>[phenyl ring]<br>—NH<br>—H | N-methyl-N-[o-(p-pivaloyloxybenzene)sulfonylaminobenzoyl]glycine | Rf 0.17<br>(chloroform:<br>methanol:<br>acetic acid =<br>100:5:1) | (CDCl₃ + CD₃OD + D₂O)<br>δ 7.8(2H,d),<br>7.8~7.5(1H,b),<br>7.1(2H,d),<br>7.4~7.04(4H,m),<br>4.1(2H,s),<br>2.7(3H,s),<br>1.35(9H,s) |
| 2(123) | CONHCHCOOH<br>CH₂<br>[phenyl rings]<br>—NH<br>—H | N-[o-(p-pivaloyloxybenzene)sulfonylaminobenzoyl]-L-phenylalanine | Rf 0.36<br>(chloroform:<br>methanol:<br>acetic acid =<br>100:5:1) | (CDCl₃ + CD₃OD)<br>δ 7.7(2H,d),<br>7.6(1H,d),<br>7.05(2H,d),<br>7.4~6.8(8H,m),<br>4.8(1H,b),<br>3.2(2H,m),<br>1.35(9H,s) |

TABLE IV-continued

| | | | |
|---|---|---|---|
| 2(124) | N-[o-(p-pivaloyloxybenzene)sulfonylaminobenzoyl]-D-phenylalanine 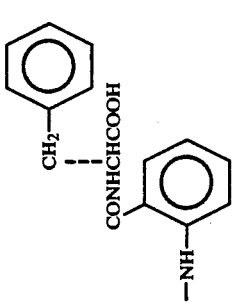 —H | Rf 0.36 (Chloroform: methanol: acetic acid = 100:5:1) | (CDCl₃ + CD₃OD) δ 7.7(2H,d), 7.6(1H,d), 7.05(2H,d), 7.4~6.8(8H,m), 4.8(1H,b), 3.2(2H,m), 1.35(9H,s) |
| 2(125) | N-[o-(p-pivaloyloxybenzene)sulfonylaminobenzoyl]-L-tryptophan 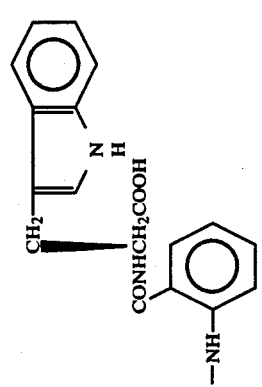 —H | Rf 0.25 (chloroform: methanol: acetic acid = 100:5:1) | (CDCl₃ + CD₃OD) δ 7.75(2H,d), 7.6(1H,d), 7.0(2H,d), 7.6~6.8(8H,m), 4.85(1H,b), 3.35(2H,d), 1.35(9H,s) |
| 2(126) | N-[o-(N-methyl-N-(p-pivaloyloxybenzene)sulfonylaminobenzoyl)]glycine 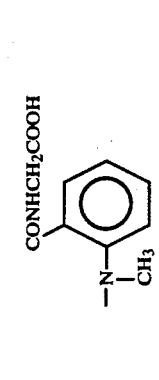 —H | Rf 0.46 (chloroform: methanol:THF = 30:3:1) | ν 3391,2977,1756, 1662,1597,1535, 1482,1405 |
| 2(127) | dl-3-phenyl-3-[o-(p-pivaloyloxybenzenesulfonylaminobenzoyl]amino propionic acid 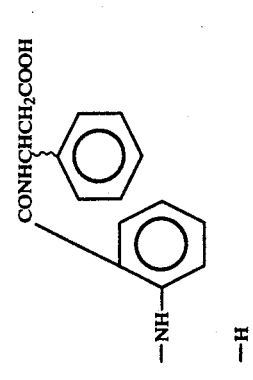 —H | Rf 0.5 (Chloroform: methanol: acetic acid = 100:5:1) | (CDCl₃ + CD₃OD) δ 7.6(2H,d), 7.7~7.5(1H,m), 7.5~7.1(7H,m), 7.0(1H,d,d), 6.9(2H,b), 5.5(1H,b), 2.9(2H,d), 1.135(9H,s) |

TABLE IV-continued

| | | | | |
|---|---|---|---|---|
| 2(128) | ![structure with COOH piperidine and NH-phenyl-CON] —H | N-[o-(p-pivaloyloxybenzene)sulfonylaminobenzoyl]-4-piperidine carboxylic acid | Rf 0.5 (chloroform: methanol: acetic acid = 100:5:1) | (CDCl$_3$ + CD$_3$OD) δ 7.7(1H,d), 7.6~7.4(1H,m), 7.4~7.2(1H,m), 7.2~6.9(4H,m), 4.0~3.6(1H,b), 2.9~2.44(4H,b), 2.0~1.44(4H,b), 1.35(9H,s) |
| 2(129) | (CH$_2$)$_2$SCH$_3$ CONHCHCOOH ![phenyl-NH] —H | N-[o-(p-pivaloyloxybenzene)sulfonylaminobenzoyl]-D-methionine | Rf 0.45 (chloroform: methanol acetic acid = 100:5:1) | (CDCl$_3$ + CD$_3$OD) δ 7.8(2H,d), 7.7~7.1(4H,m), 7.1(2H,d), 4.7(1H,b), 2.9(3H,s), 2.6~1.9(4H,m), 1.35(9H,s) |
| 2(130) | CH(CH$_3$)$_2$ CONHCHCOOH ![phenyl-NH] —H | N-[o-(p-pialoyloxybenzene)sulfonylaminobenzoyl]-D-valie | Rf 0.46 (ethyl acetate: n-hexane: acetic acid = 10:10:0.5) | ν 3392,2973,1746, 1641,1595,1528, 1493,1398 |
| 2(131) | CONH(CH$_2$)$_3$COOH ![phenyl-NH] —H | p[N-(o-caroxypropylcarbamoylphenyl)sulfamoyl]phenyl ester of pivalic acid | Rf 0.36 (chloroform: methanol: acetic acid = 100:5:1) | (CDCl$_3$ + CD$_3$OD) δ 7.7(2H,d), 7.7~7.5(1H,b), 7.4~7.2(2H,m), 7.0(2H,d),7.1 (1H,d),3.3(2H,t), 2.4(2H,t),1.9 (2H,q),1.35(9H,s) |
| 2(132) | CONH(CH$_2$)$_5$COOH ![phenyl-NH] —H | p-[N-(o-carboxyheptylcarbamoylphenyl)sulfamoyl]phenyl ester of pivalic acid | Rf 0.38 (chloroform: methanol acetic acid = 100:5:1) | (CDCl$_3$ + CD$_3$OD) δ 7.7(2H,d), 7.7~7.6(1H,b), 7.4~7.2(2H,m), 7.0(2H,d),7.1 (1H,b),3.2(2H,b), 2.3(2H,b),1.9~1.2 (6H,b),1.35(9H,s) |

TABLE IV-continued

| | | | |
|---|---|---|---|
| 2(133) | N-[o-[(p-pivaloyloxybenzene)sulfonylaminobenzoyl]-D-alanine  —H | Rf 0.28 (chloroform: methanol acetic acid = 100:5:1) | (CDCl$_3$ + CD$_3$OD)) δ 7.75(2H,d), 7.8∼7.7(1H,b), 7.5∼7.4(2H,m), 7.05(2H,d), 7.2∼7.1(1H,m), 4.6(1H,m), 1.5(3H,d), 1.35(9H,s) |
| 2(134) | N-[(p-pivaloyloxybenzene)sulfonyl]-4-piperidine carboxylic acid  —H | Rf 0.4 (chloroform: methanol acetic acid = 100:5:1) | (CDCl$_3$) δ 7.75(2H,d), 7.2(2H,d), 3.6(2H,b), 2.7∼2.0(3H,m), 2.0∼1.6(4H,m), 1.20(9H,s) |
| 2(135) | 4-[(p-pivaloylamino]-2-naphtoic acid  —H | Rf 0.4 (chloroform: methanol acetic acid = 100:5:1) | (CDCl$_3$) δ 8.9(1H,d), 8.1(1H,d), 7.75(2H,d), 8.0∼7.8(1H,b), 7.6∼7.3(3H,m), 7.0(2H,d), 1.35(9H,s) |

*The number of the carbon atoms of benzene ring were named from a carbon atom combined with the oxygen atom in pivaloyl group as first.

TABLE V

Structure:
(CH₃)₃C—C(=O)—O—[phenyl ring positions 1,2,3,4 with (R³)ₘ]—CO—N(R¹)(R²)

| Example No. | —N(R¹)(R²), —R³* | Name | TLC | IR (cm⁻¹) or NMR |
|---|---|---|---|---|
| 2(108) | —NH—(phenyl-CH₃), 2-Cl | 2-chloro-4-[N-(p-tolyl)carbamoyl] phenyl ester of pivalic acid | Rf 0.77 (methylene chloride: acetic acid = 30:1) | (CDCl₃) δ 7.5(2H,b), 7.2~6.5(5H,m), 6.2(2H,b), 2.1(3H,s), 1.3(9H,s) |
| 2(109) | —NH—(phenyl-CH₃), 2-OCH₃ | 2-methoxy-p-[N-(p-tolyl)carbamoyl] phenyl ester of pivalic acid | Rf 0.74 (methylene chloride: acetic acid = 30:1) | ν 3200,2980,1750, 1640,1600,1510, 1400,1330,1280, 1110 |
| 2(110) | —NH—(phenyl-COOCH₂-phenyl), —H | 4-[N-(o-benzyloxycarbonylphenyl) carbamoyl]phenyl ester of pivalic acid | Rf 0.83 (methylene chloride: acetic acid = 30:1) | |
| 2(111) | —NH—(2-pyridyl), —H | 4-[N-(2-pyridyl)carbamoyl]phenyl ester of pivalic acid | Rf 0.30 (chloroform: methanol = 10:1) | |
| 2(112) | —N(CH₃)(phenyl), 3-OCOCH₃ | 3-acetyloxy-4-[(N-methyl-N-phenyl) carbamoyl]phenyl ester of pivalic acid | Rf 0.24 (methylene chloride: acetic acid = 30:1) | (CHDl₃) δ 7.1~7.5(6H,m), 6.7~7.0(2H,m), 3.5(3H,s), 2.3(3H,s), 1.3(9H,s) |
| 2(113) | —NH—(phenyl-COOCH₂-phenyl), —H | 4-[N-(m-benzyloxycarbonylphenyl) carbamoyl]phenyl ester of pivalic acid | Rf 0.38 (methylene chloride: acetic acid = 30:1) | |

EXAMPLE 3 p-[N-(p-(p-guanidinobenzoyloxy)phenyl)sulfamoyl]-phenyl ester of pivalic acid

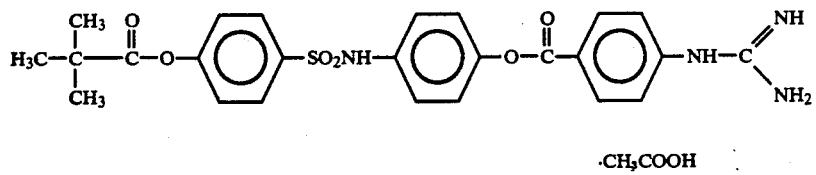

·CH₃COOH p-Guanidinobenzoyl chloride hydrochloride (800 mg) was added to pyridine solution (5 ml) of the compound of the present invention (500 mg) obtained in Example 2(7) under cooling with ice, and the mixture was stirred for 2 hours.

After reaction, ether was added to the reaction mixture and the supernatant was decanted. Saturated aqueous solution of sodium bicarbonate was added to the residue to obtain oily carbonate.

Further, the supernatant was decanted and the residue was purified by column chromatography on silicagel (ethyl acetate : acetic acid : water =400 : 100 : 30) to give the title compound (532 mg) having the following physical data.

TLC : Rf 0.80 (ethyl acetate: acetic acid : water=3:1:1);

IR: $\nu$3600~2300, 1750~1700, 1680, 1500, 1400.

EXAMPLE 4 p-[N-(p-benzyloxycarbonylphenyl)sulfamoyl]phenyl ester of pivalic acid

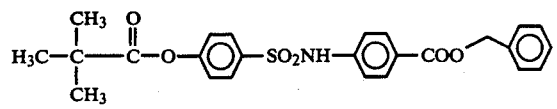

The title compound (210 mg, same as compound obtained in Example 1(5) was obtained by the same procedure as Reference Example 1→Example 1, by using a corresponding sulfonylchloride compound as starting material.

The compounds of the present invention were obtained by the same procedure as Example 4, by using a corresponding amine and pivaloyl chloride.

TABLE VI (CH₃)₃C—COO—[phenyl with positions 1,2,3,4 and (R³)ₘ]—SO₂N(R¹)(R²)

| Example No. | —N(R¹)(R²) | —R³* | Name | TLC | IR (cm⁻¹) or NMR |
|---|---|---|---|---|---|
| 4(1) | —NH—CH(COOCH₂-phenyl)(CH₂-phenyl) | —H | p-[N-((1-benzyloxycarbonyl-1-benzyl)methyl)sulfamoyl]phenyl ester of pivalic acid | Rf 0.47 (hexane: ethyl acetate = 5:2) | |
| 4(2) | —NH—CH(COOCH₂-phenyl)(phenyl) | —H | p-[N-((1-benzyloxycarbonyl-1-phenyl)methyl)sulfamoyl]phenyl ester of pivalic acid | Rf 0.40 (hexane: ethyl acetate = 5:2) | |

TABLE VI-continued (CH₃)₃C—COO—[phenyl(1,2,3,4 positions)]—SO₂N(R¹)(R²), (R³)ₘ

| Example No. | —N(R¹)(R²) / —R³* | Name | TLC | IR (cm⁻¹) or NMR |
|---|---|---|---|---|
| 4(3) | —NH—(o-COOCH₂Ph phenyl) ; —H | p-[N-((o-benzyloxycarbonyl)phenyl)sulfamoyl]phenyl ester of pivalic acid | Rf 0.62 (hexane: ethyl acetate = 5:2) | |
| 4(4) | —NH—(o-COOCH₂Ph phenyl) ; 2-CH₃ | 2-methyl-4-[N-((o-benzyloxycarbonyl)phenyl)sulfamoyl]phenyl ester of pivalic acid | Rf 0.62 (hexane: ethyl acetate = 5:2) | |
| 4(5) | —NH—(CH₂)₂—Ph ; —H | p-(N-phenethylsulfamoyl)phenyl ester of pivalic acid | Rf 0.41 (hexane: ethyl acetate = 5:2) | δ 7.85(2H,d), 7.4~7.0(7H,m), 4.5~4.2(1H,b), 3.4~3.1(2H,m), 2.8(2H,t), 1.35(9H,s) |
| 4(6) | —NH—CH₂—Ph ; —H | p-(N-benzylsulfamoyl)phenyl ester of pivalic acid | Rf 0.47 (hexane: ethyl acetate = 5:2) | δ 7.9(2H,d), 7.4~7.2(7H,m), 4.7(1H,b), 4.2(2H,d), 1.35(9H,s) |

EXAMPLE 5 p-[N-(p-carboxyphenyl)sulfamoyl]phenyl ester of pivalic acid

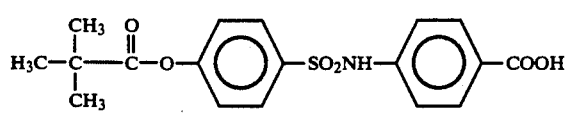

In an atmosphere of hydrogen gas, the mixture solution of benzyl compound (190 mg) of Example 4, 10% Pd-carbon (30 mg), acetic acid (10 ml) and THF (4 ml) was stirred for 3 hours at room temperature.

The reaction solution was filtered off, and the filtrate was carried out azeotropic concentration by mixture of toluene-THF, and the azeotropic concentrate was recrystallized by mixture of ethyl acetate-hexane to give title compound (143 mg) having the following physical data.

TLC: Rf 0.56 (ethyl acetate: hexane=1:1);
IR: ν2700~2400, 1750, 1680, 1600, 1340, 1290, 1200, 1160, 1110 cm⁻¹.

Hereinafter, by the same procedure of Example 5, using corresponding benzyl compound, compounds of the present invention described in the following Table VII were obtained.

TABLE VII

Structure for all entries:

$(CH_3)_3C-C(=O)-O-$[phenyl ring positions 1,2,3,4]$-SO_2N(R^1)(R^2)$ with $(R^3)_m$ substituent

| Example No. | —R³* | Name | TLC | IR (cm⁻¹) or NMR |
|---|---|---|---|---|
| 5(1) | —NH—CH(COOH)—CH₂—C₆H₅; —H | p-[N-(α-carboxyphenethyl)sulfamoyl] phenyl ester of pivalic acid | Rf 0.34 chloroform: methanol: acetic acid = 100:5:1 | δ 7.8(2H,d), 7.4~7.0(7H,m), 5.2(1H,b), 4.2(1H,b), 3.2~3.0(2H,b), 1.4(9H,s) |
| 5(2) | —NH—CH(COOH)—C₆H₅; —H | p-[N-(α-carboxybenzyl)sulfamoyl] phenyl ester of pivalic acid | Rf 0.44 (chloroform: methanol: acetic acid = 100:5:1) | δ 7.8(2H,d), 7.35(5H,bs), 7.15(2H,d), 5.75(1H,d), 5.15(1H,d), 1.35(9H,s) |
| 5(3) | N-methyl-anthranilic type: —NH-C₆H₄(o-COOH); —H | p-[N-(o-carboxyphenyl)sulfamoyl] phenyl ester of pivalic acid | Rf 0.37 (chloroform: methanol: acetic acid = 100:5:1) | δ 8.2~7.0(8H,m), 5.5(1H,b), 1.35(9H,s) |
| 5(4) | —NH—C₆H₄(o-COOH); 2-CH₃ | 2-methyl-4-[N-(o-carboxyphenyl)sulfamoyl]phenyl ester of pivalic acid | Rf 0.25 (chloroform: methanol: acetic acid = 100:5:1) | δ 8.05(1H,d), 7.9~7.3(5H,m), 7.3~7.0(2H,m), 2.2(3H,s), 1.35(9H,s) |
| 5(5) | —NH—C₆H₃(2-COOH)(4-Cl); 2-CH₃ | 2-methyl-4-[N-(2-carboxy-4-chlorophenyl)sulfamoyl]phenyl ester of pivalic acid | Rf 0.26 (chloroform: methanol: acetic acid = 100:5:1) | (CDCl₃ + CD₃OD) δ 8.0(1H,d), 7.8~7.6(3H,m), 7.45(1H,d,d), 7.1(1H,d), 2.2(3H,s), 1.4(9H,s) |
| 5(6) | —NH—C₆H₃(2-COOH)(4-CH₃); 2-CH₃ | 2-methyl-4-[N-(2-carboxy-4-methylphenyl)sulfamoyl]phenyl ester of pivalic acid | Rf 0.41 (chloroform: methanol: acetic acid = 100:5:1) | (CDCl₃) δ 7.9~7.5(4H,m), 7.38(1H,d), 7.1(1H,d), 2.35(3H,s), 2.2(3H,s), 1.35(9H,s) |
| 5(7) | —NH—C₆H₄(o-COOH); 2-CH(CH₃)₂ | 2-isopropyl-4-[N-(o-carboxyphenyl)sulfamoyl]phenyl ester of pivalic acid | Rf 0.32 (chloroform: methanol: acetic acid = 100:5:1) | (CDCl₃) δ 8.0(1H,d), 7.9~7.5(4H,m), 7.25(1H,d), 7.1(1H,d), 3.0(1H,b), 1.35(9H,s), 1.15(6H,d) |

TABLE VII-continued

| Example No. —R³* | (structure with N-R¹/R²) | Name | TLC | IR (cm⁻¹) or NMR |
|---|---|---|---|---|
| 5(8) | —NH—(2-COOH, 4-Cl phenyl); 2-CH(CH₃)₂ | 2-isopropyl-4-[N-(2-carboxy-4-chlorophenyl)sulfamoyl]phenyl ester of pivalic acid | Rf 0.32 (chloroform: methanol: acetic acid = 100:5:1) | (CDCl₃) δ 7.95(1H,d), 7.85~7.4(4H,m), 7.05(1H,d), 3.0(1H,b), 1.35(9H,s), 1.15(6H,d) |
| 5(9) | —NH—(2-COOH naphthyl); 2-CH₃ | 2-methyl-4-[N-(2-carboxynaphthyl)sulfamoyl]phenyl ester of pivalic acid | Rf 0.33 (chloroform: methanol: acetic acid = 100:5:1) | (CDCl₃) δ 8.6(1H,s), 8.05(1H,s), 7.9~7.3(6H,m), 7.0(1H,d), 2.1(3H,s), 1.35(9H,s) |
| 5(10) | —NH—(2-COOH, 5-COOH phenyl); 2-CH₃ | 2-methyl-4-[N-(2,5-dicarboxyphenyl)sulfamoyl]phenyl ester of pivalic acid | Rf 0.26 (chloroform: methanol: acetic acid = 30:2:1) | CDCl₃ + CD₃OD) δ 8.3(1H,d), 8.0(1H,d), 7.8~7.6(3H,m), 7.03(1H,d), 2.2(3H,s), 1.35(9H,s) |
| 5(11) | —NH—(3-COOH pyridin-2-yl); 2-CH₃ | 2-methyl-4-[N-(3-carboxypyridine-2-yl)sulfamoyl]phenyl ester of pivalic acid | Rf 0.48 (chloroform: methanol: acetic acid = 30:2:1) | (CDCl₃ + CD₃OD) δ 8.3(2H,m), 8.0(1H,s), 7.9(1H,d), 6.95(1H,d,d), 2.25(3H,s), 1.35(9H,s) |
| 5(12) | —NH—(2-COOH, 4-OH phenyl); 2-CH₃ | 2-methyl-4-[N-(2-carboxy-4-hydroxyphenyl)sulfamoyl]phenyl ester of pivalic acid | Rf 0.31 (chloroform: methanol: acetic acid = 30:2:1) | (CDCl₃ + CD₃OD) δ 7.7~7.4(3H,m), 7.32(1H,d), 7.1~6.8(2H,m), 2.15(3H,s), 1.35(9H,s) |
| 5(13) | —NH—(o-COOH phenyl); 2,6-diCH₃ | 2,6-dimethyl-4-[N-(o-carboxyphenyl)sulfamoyl]phenyl ester of pivalic acid | Rf 0.28 (ethyl acetate: hexane: acetic acid = 10:20:0.5) | ν 3500~2500, 1750, 1660, 1580, 1480, 1420, 1340, 1250, 1150, 1100 |
| 5(14) | —NH—(2-COOH, 4-OCOCH₃ phenyl); 2-CH₃ | 2-methyl-4-[N-(2-carboxy-4-acetyloxyphenyl)sulfamoyl]phenyl ester of pivalic acid | Rf 0.33 (chloroform: methanol: acetic acid = 100:5:1) | (CDCl₃) δ 7.8~7.1(5H,m), 7.0(1H,d), 2.3(3H,s), 2.15(3H,s), 1.35(9H,s) |

TABLE VII-continued

| Example No. −R³* (with −N(R¹)(R²)) | Name | TLC | IR (cm⁻¹) or NMR |
|---|---|---|---|
| 5(15) −NH—C₆H₃(2-CH₃)(4-OCO(CH₂)₄CH₃), R³=COOH | 2-methyl-4-[N-(2-carboy-4-hexanoyloxyphenyl)sulfamoyl] phenyl ester of pivalic acid | Rf 0.33 (chloroform: methanol: acetic acid = 100:5:1) | (CDCl₃) δ 7.75~7.40(4H,m), 7.15(1H,d,d), 6.95(1H,d), 2.45(2H,t), 2.1(3H,s), 1.35(9H,s), 0.85(3H,t) |
| 5(16) −NH—C₆H₃(2-CH₃), R³=COOH, COOH | 2-methyl-4-[N-(2,5-dicarboxyphenyl)sulfamoyl]phenyl ester of pivalic acid | Rf 0.37 (chloroform: methanol: acetic acid = 30:3:1) | ((CD₃)₂SO) δ 7.98(2H,d), 7.4~7.2(3H,m), 7.0(1H,d), 2.1(3H,s), 1.36(9H,s) |
| 5(17) −NH—C₆H₃(2-CH₃), R³=COOCH₂COOH | o-(3-methyl-4-pivaloyloxybenzene)sulfonylaminobenzoyloxy acetic acid | Rf 0.33 (chloroform: methanol: acetic acid = 100:5:1) | (CDCl₃) δ 8.0~6.85(7H,m), 4.75(2H,s), 2.15(3H,s), 1.35(9H,s) |

$$(CH_3)_3C-\underset{\underset{O}{\|}}{C}-O-\underset{(R^3)_m}{\bigcirc}-CON\underset{R^2}{\overset{R^1}{\diagdown}}$$

| Example No. | Name | TLC | IR (cm⁻¹) or NMR |
|---|---|---|---|
| 5(18) −NH—C₆H₄—COOH ; −H | p-[N-(o-carboxyphenyl)carbamoyl] phenyl ester of pivalic acid | Rf 0.42 (ethyl acetate: hexane: acetic acid = 10:20:0.5) | ν 1740,1680,1660, 1600,1590,1540, 1480,1440 |
| 5(19) −N(CH₃)—C₆H₄—COOH (o) ; −H | p-[N-(methyl-N-(o-carboxyphenyl)carbamoyl]phenyl ester of pivalic acid | Rf 0.17 (ethyl acetate: hexane: acetic acid = 10:20:0.5) | ν 1750,1720,1590, 1470,1440,1380 |
| 5(20) −N(CH₃)—C₆H₄—COOH (m) ; −H | p-[N-(methyl-N-(m-carboxyphenyl)carbamoyl]phenyl ester of pivalic acid | Rf 0.15 methylene chloride: ethyl acetate = 30:1) | ν 1750,1720,1640, 1600,1580,1480, 1440,1370 |

EXAMPLE 6 p-[(N-methyl-N-phenyl)sulfamoyl]phenyl ester of pivalic acid

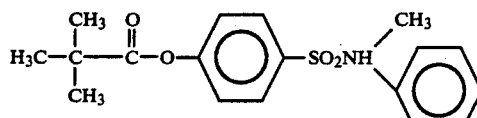

In an atmosphere of argon, THF solution (8 ml) of the compound of the present invention of Example 1 (1) (300 mg) was added to sodium hydride (37 mg) under cooling with ice, and the mixture was stirred for 2 hours.

Methyl iodide (66 μl) and hexamethylphosphoramide (HMPA) (1 ml) were added to the reaction solution, and the mixture was stirred for 30 minutes.

The reaction solution was extracted with ether, and the extract was washed with successive, water and saturated aqueous solution of sodium chloride.

And further, the solution was dried with sodium sulfate, and distilled off under reduced pressure to give the title compound (180 mg) having the following physical data.

TLC: Rf 0.61 (methylene chloride : ethyl acetate = 30:1);

IR: ν1750, 1590, 1490, 1450, 1340 cm$^{-1}$.

Hereinafter, by the same procedure of Example 6, using corresponding derivative of pivlaic acid, the compounds of the present invention described in Table VIII were obtained.

TABLE VIII $$(CH_3)_3C-\overset{O}{\overset{\|}{C}}-O-\underset{R^3}{\overset{2\ \ 3}{\underset{}{\bigcirc}}}-CON\overset{R^1}{\underset{R^2}{}}$$

| Example No. | $-N\overset{R^1}{\underset{R^2}{}}$  $-R^{3*}$ | Name | TLC | IR (cm$^{-1}$) or NMR |
|---|---|---|---|---|
| 6(1) | $-N\overset{CH_3}{\underset{}{}}-\bigcirc-CH_3$ <br> —H | p-[N-methyl-N-(p-tolyl)carbamoyl] phenyl ester of pivalic acid | Rf 0.33 (methylene chloride: acetic acid = 30:1) | ν 1750,1640,1600, 1510,1360,1200, (neat) |
| 6(2) | $-N\overset{CH_3}{\underset{}{}}-\bigcirc-COOCH_2-\bigcirc$ <br> —H | p-[N-methyl-N-(o-benzyloxy-carbonylphenyl)carbamoyl]phenyl ester of pivalic acid | Rf 0.21 (methylene chloride: acetic acid = 30:1) | ν 1750,1720,1640, 1600,1370,1250, (neat) |
| 6(3) | $-N\overset{CH_3}{\underset{}{}}-\bigcirc-COOCH_2-\bigcirc$ <br> —H | p-[N-methyl-N-(m-benzyloxycarbonylphenyl)carbamoyl] phenyl ester of pivalic acid | Rf 0.38 (methylene chloride: acetic acid = 30:1) | |
| 6(4) | $-N\overset{CH_3}{\underset{}{}}-\bigcirc_N$ <br> —H | p-[N-methyl-N-(pyridine-3-yl) carbamoyl]phenyl ester of pivalic acid | Rf 0.44 (chloroform: methanol = 10:1) | ν 1750,1650,1480, 1420,1380,1200, 1110 |

EXAMPLE 7

3-hydroxy-4-[(N-methyl-N-pheyl)scarbamoyl]phenyl ester of pivalic acid

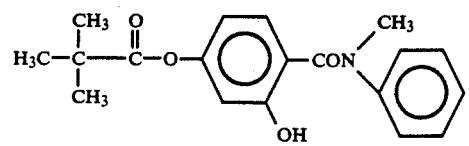

The mixture of methanol (5 ml) and triethylamine (0.3 ml) of the compound (83 mg) of the present invention obtained by procedure of Example 2 (112) was stirred for 3 hours at room temperature.

The reaction solution was extracted with ether, and the extract was washed successively with 1N-HCl, water, saturated an aqueous solution of sodium chloride.

The solution was dried with sodium sulfate, and distilled off under reduced pressure to give the title compound (68 mg) having the following physical data.

TLC : Rf 0.34 (methylene chloride:ethyl acetate=30:1);

NMR (CDCl3): δ7.0~7.4(6H, m), 6.65(1H,d), 6.1(1H,2d), 3.5(3H,s), 1.3(9H,s).

EXAMPLES OF PREPARATIONS

The following components were admixed in conventional method and punched out to obtain 100 tablets each containing 50 mg of active ingredient.

| | |
|---|---|
| N-[o-(p-pivaloyloxybenzene)sulfonylaminobenzoyl]glycine | 5 g |
| Cellulose calcium glycolate (disintegrating agent) | 0.2 g |
| Magnesium stearate (lubricating agent) | 0.1 g |
| Microcrystaline cellulose | 4.7 g |

What is claimed is:
1. A compound of the formula:

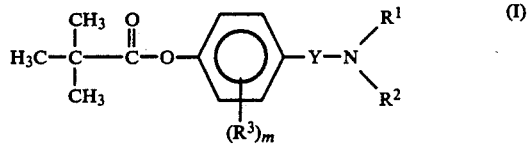

wherein Y represents a sulfonyl (—SO$_2$) group,
R$^1$ and R$^2$, which may be the same or different, each represent,
  (1) a hydrogen atom, or
  (2) an alkyl group of up to 16 carbon atoms;
R$^3$ represents
  (1) a hydrogen atom, or
  (2) an alkyl group of up to 6 carbon atoms; and
m represents an integer of up to 4;
or non-toxic salts or acid addition salts thereof.

2. A compound according to claim 1, which is p-(N-tertbutylsulfamoyl)phenyl ester of pivalic acid.

3. A pharmaceutical composition for the prevention and treatment of pulmonary emphysema, atherosclerosis and rheumatoid arthritis, which comprises, as active ingredient, an effective amount of at least one compound of the formula (I) depicted in claim 1 wherein the various symbols are as defined in claim 1, and a pharmaceutically acceptable carrier.

* * * * *